(12) United States Patent
Belef et al.

(10) Patent No.: US 6,475,226 B1
(45) Date of Patent: Nov. 5, 2002

(54) PERCUTANEOUS BYPASS APPARATUS AND METHOD

(75) Inventors: William M. Belef, San Jose, CA (US); Eric M. DoBrava, Crystal, MN (US); Joseph D. Farrell, Minneapolis, MN (US); Jaydeep Y. Kokate, Maple Grove, MN (US); Daniel M. LaFontaine, Plymouth, MN (US); Brian J. Lowe, Fridley, MN (US); Jonathan C. Sell, West St. Paul, MN (US); Bradley F. Slaker, Greenfield, MN (US); David A. White, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/243,729

(22) Filed: Feb. 3, 1999

(51) Int. Cl.⁷ .................................. A61B 17/00
(52) U.S. Cl. ...................... 606/185; 606/170
(58) Field of Search .................... 606/1, 108, 159, 606/170, 171, 180; 604/22; 60/562–568

(56) References Cited

U.S. PATENT DOCUMENTS

| | | | |
|---|---|---|---|
| 5,409,019 A | 4/1995 | Wilk | 128/898 |
| 5,702,412 A * | 12/1997 | Popov et al. | 606/159 |
| 5,830,222 A * | 11/1998 | Makower | 606/159 |
| 5,836,311 A | 11/1998 | Borst et al. | 128/897 |
| 5,855,210 A | 1/1999 | Sterman et al. | 128/898 |
| 5,855,614 A | 1/1999 | Stevens et al. | 623/11 |
| 5,868,770 A | 2/1999 | Rygaard | 606/167 |
| 5,893,369 A | 4/1999 | LeMole | 606/184 |
| 5,895,404 A | 4/1999 | Ruiz | 606/185 |
| 5,904,147 A | 5/1999 | Conlan et al. | 128/899 |
| 5,904,690 A | 5/1999 | Middleman et al. | 606/113 |
| 5,910,150 A * | 6/1999 | Saadat | 604/22 |
| 5,921,979 A | 7/1999 | Kovac et al. | 606/1 |
| 5,928,181 A | 7/1999 | Coleman et al. | 604/8 |
| 5,944,019 A | 8/1999 | Knudson et al. | 128/898 |
| 5,947,125 A | 9/1999 | Benetti | 128/898 |
| 5,947,919 A | 9/1999 | Krueger et al. | 604/8 |
| 6,068,638 A * | 5/2000 | Makower | 606/170 |
| 6,102,926 A * | 8/2000 | Tartaglia et al. | 606/170 |
| 6,190,353 B1 | 2/2001 | Makower et al. | 604/95 |

FOREIGN PATENT DOCUMENTS

| | | |
|---|---|---|
| WO | WO 92/10142 | 6/1992 |
| WO | 0 629 382 A1 | 12/1994 |
| WO | WO 97/27897 | 8/1997 |
| WO | WO 98/19614 | 5/1998 |
| WO | WO 98/19625 | 5/1998 |

(List continued on next page.)

Primary Examiner—David O. Reip
(74) Attorney, Agent, or Firm—Westman, Champlin & Kelly, P.A.

(57) ABSTRACT

Devices and methods for percutaneous translumenal minimally invasive coronary surgery, particularly bypass surgery involving the following basic steps: determining a proper location for treatment, navigating a suitable device to the treatment site, creating an extravascular opening and pathway, guiding and/or monitoring the progress of creating the opening and pathway, and maintaining the extravascular opening and pathway. One or more extravascular openings and/or pathways may be created to define a fluid path or bypass around the vascular restriction. For example, an intravascular catheter for creating an extravascular opening in a vessel wall includes an elongate shaft adapted for intravascular navigation, an anchoring mechanism disposed on the distal end of the shaft, and a tissue penetrating member having a proximal end slidably disposed in the shaft and a distal end including a tissue penetrating mechanism.

35 Claims, 32 Drawing Sheets

FOREIGN PATENT DOCUMENTS

| | | |
|---|---|---|
| WO | WO 98/51223 | 11/1998 |
| WO | WO 98/52475 | 11/1998 |
| WO | WO 98/57590 | 12/1998 |
| WO | WO 98/57591 | 12/1998 |
| WO | WO 98/57592 | 12/1998 |
| WO | WO 99/04836 | 2/1999 |
| WO | WO 99/04845 | 2/1999 |
| WO | WO 99/17683 | 4/1999 |
| WO | WO 99/18887 | 4/1999 |
| WO | WO 99/35975 | 7/1999 |
| WO | WO 99/35977 | 7/1999 |
| WO | WO 99/35978 | 7/1999 |
| WO | WO 99/35979 | 7/1999 |
| WO | WO 99/35980 | 7/1999 |
| WO | WO 99/36000 | 7/1999 |
| WO | WO 99/36001 | 7/1999 |
| WO | WO 99/38459 | 8/1999 |
| WO | WO 99/40853 | 8/1999 |
| WO | WO 99/40868 | 8/1999 |
| WO | WO 99/42160 | 8/1999 |

\* cited by examiner

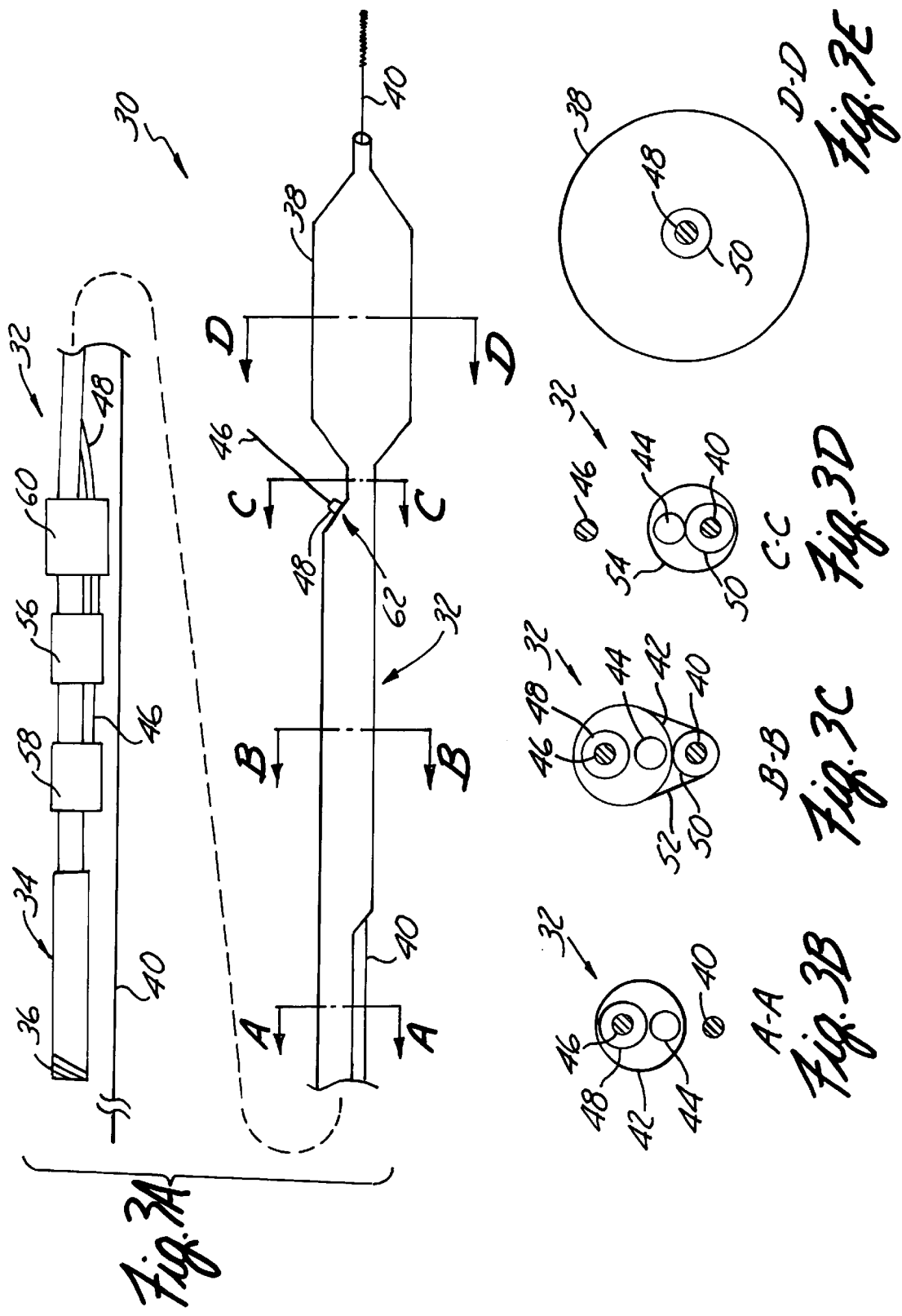

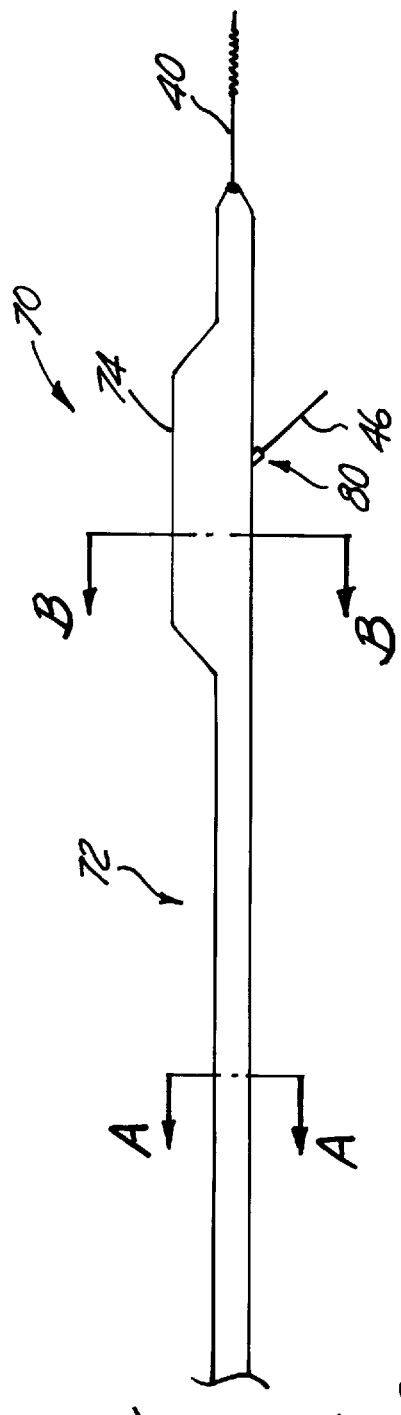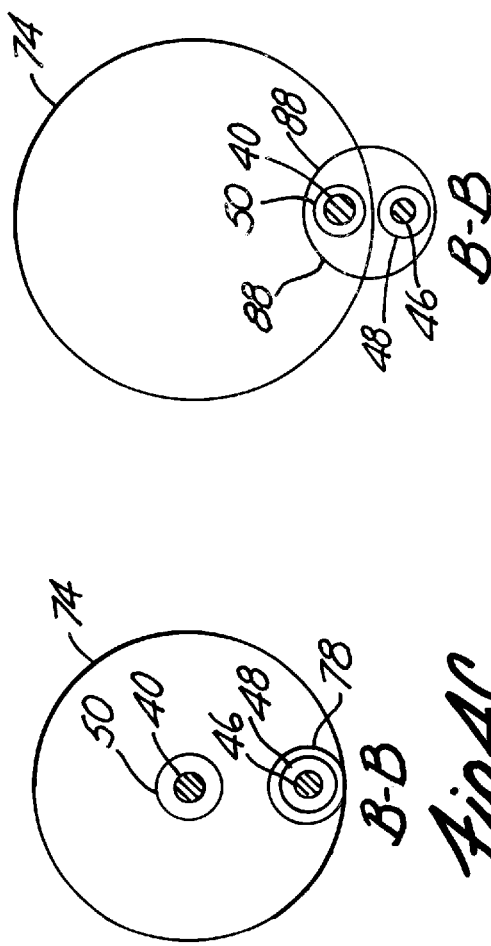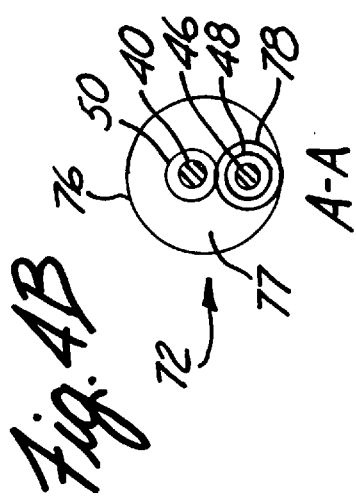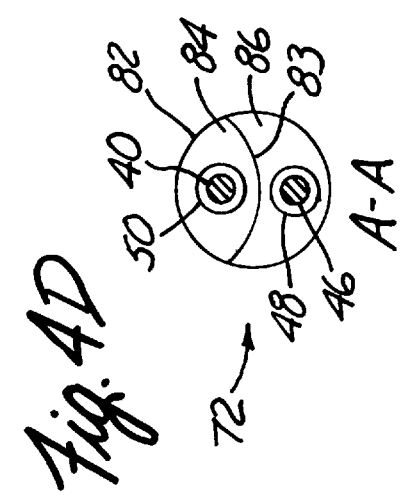

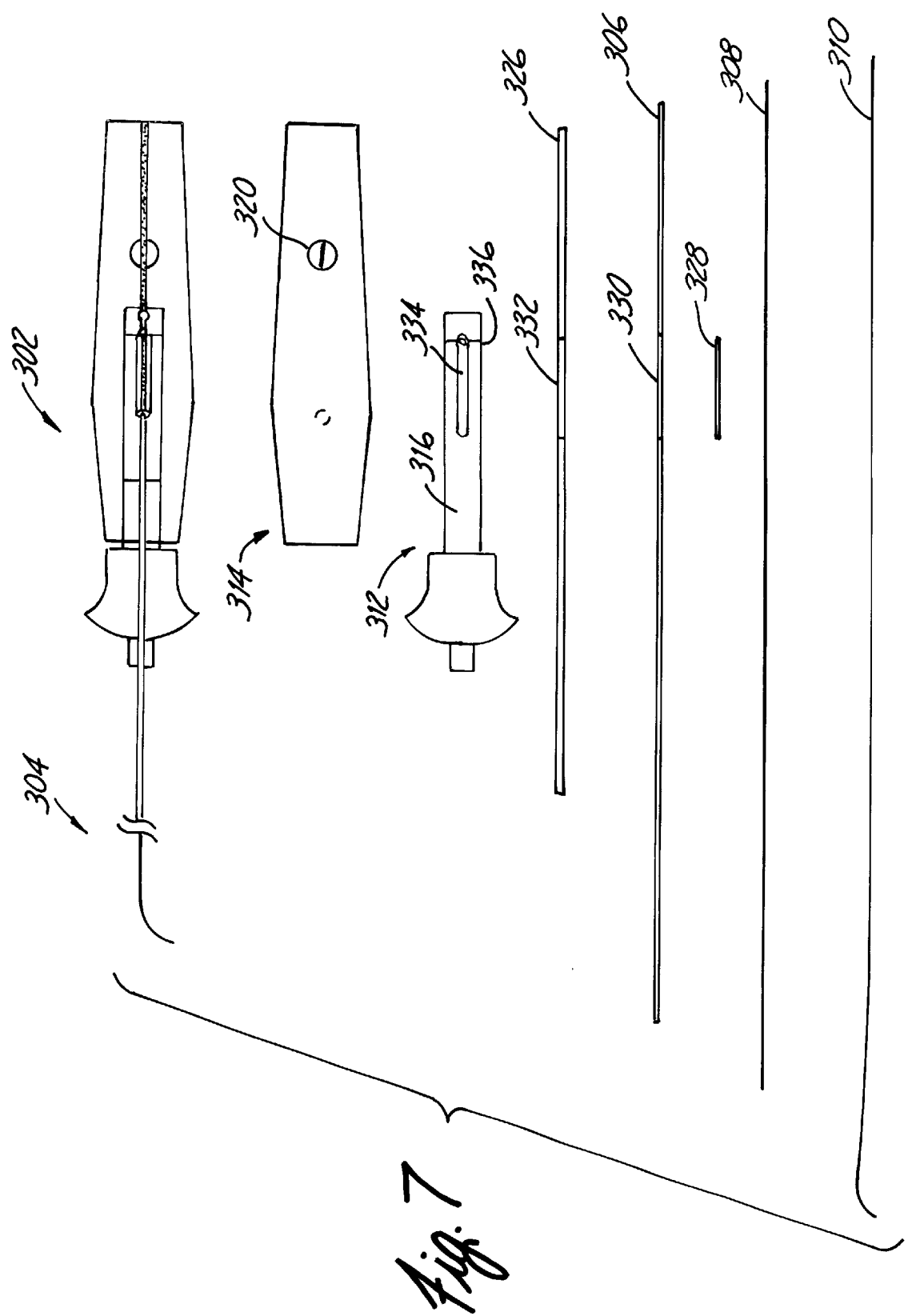

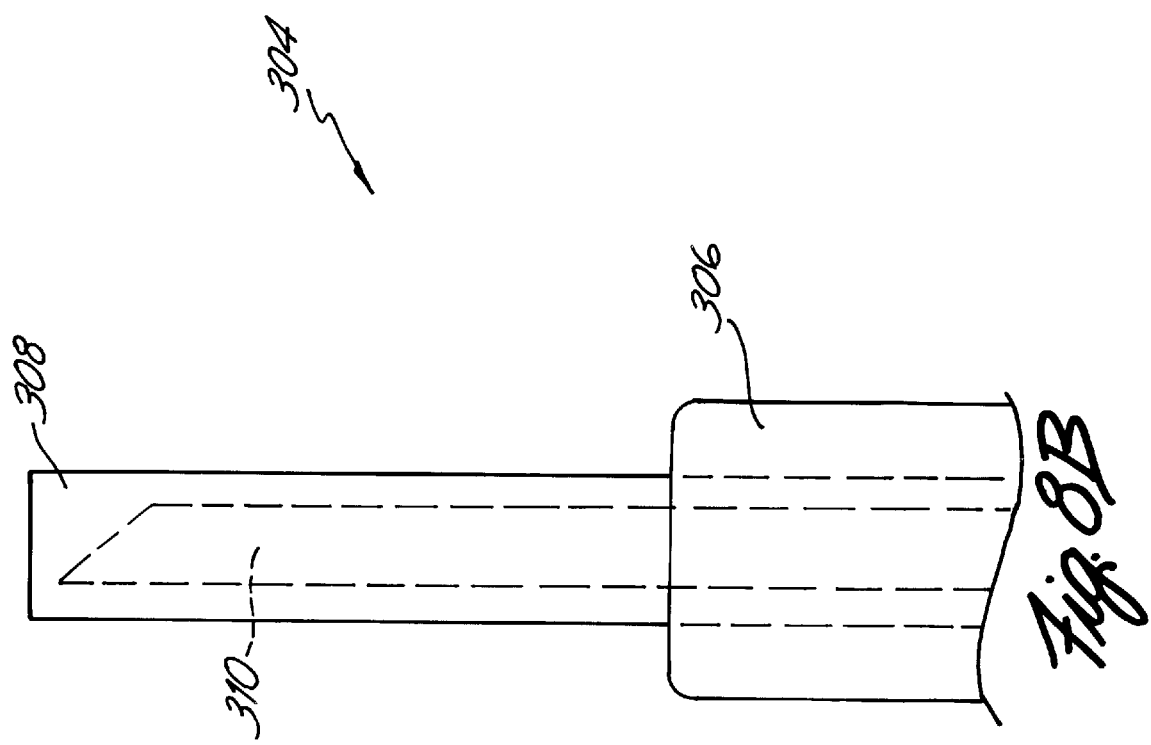
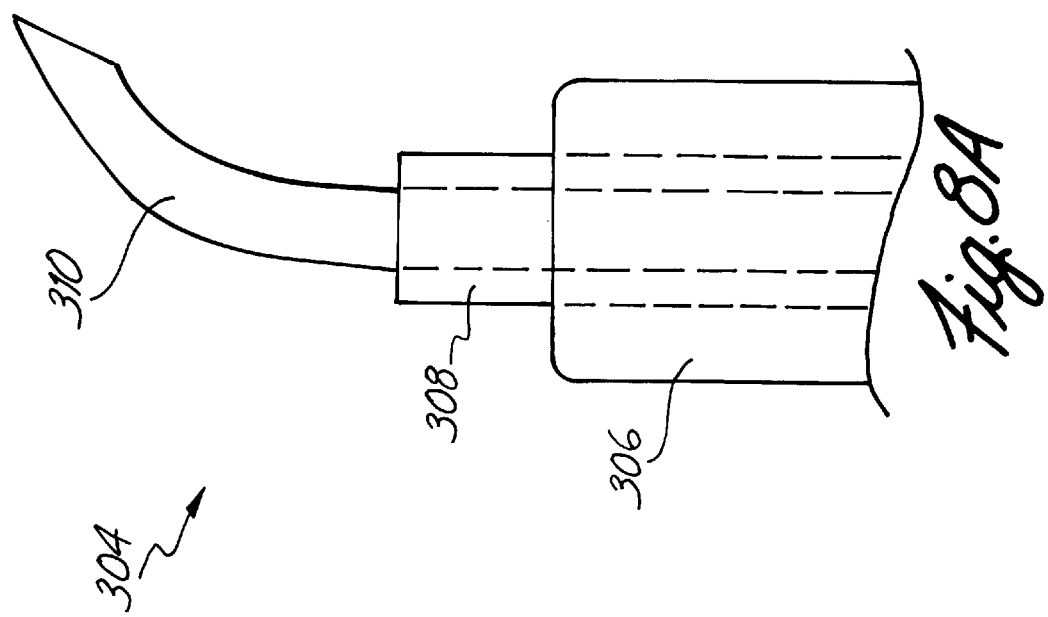

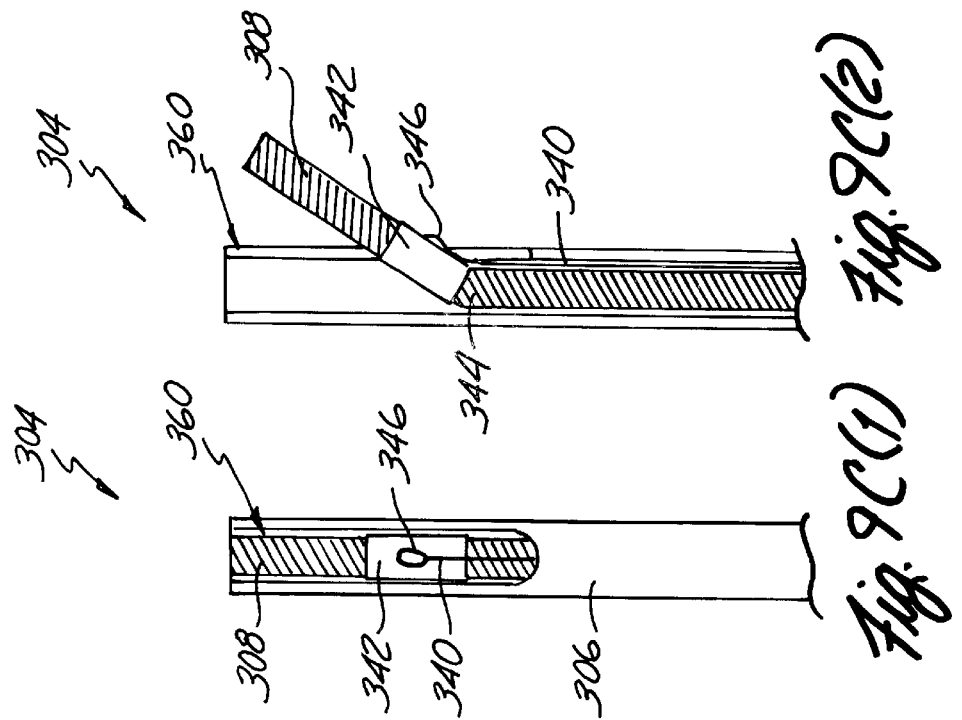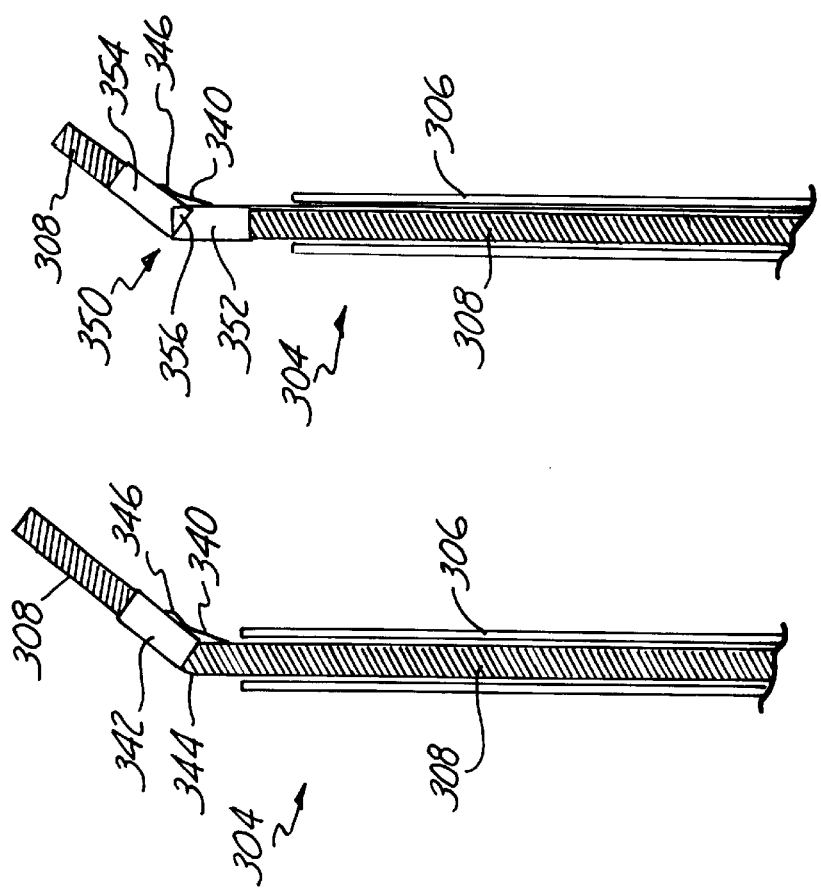

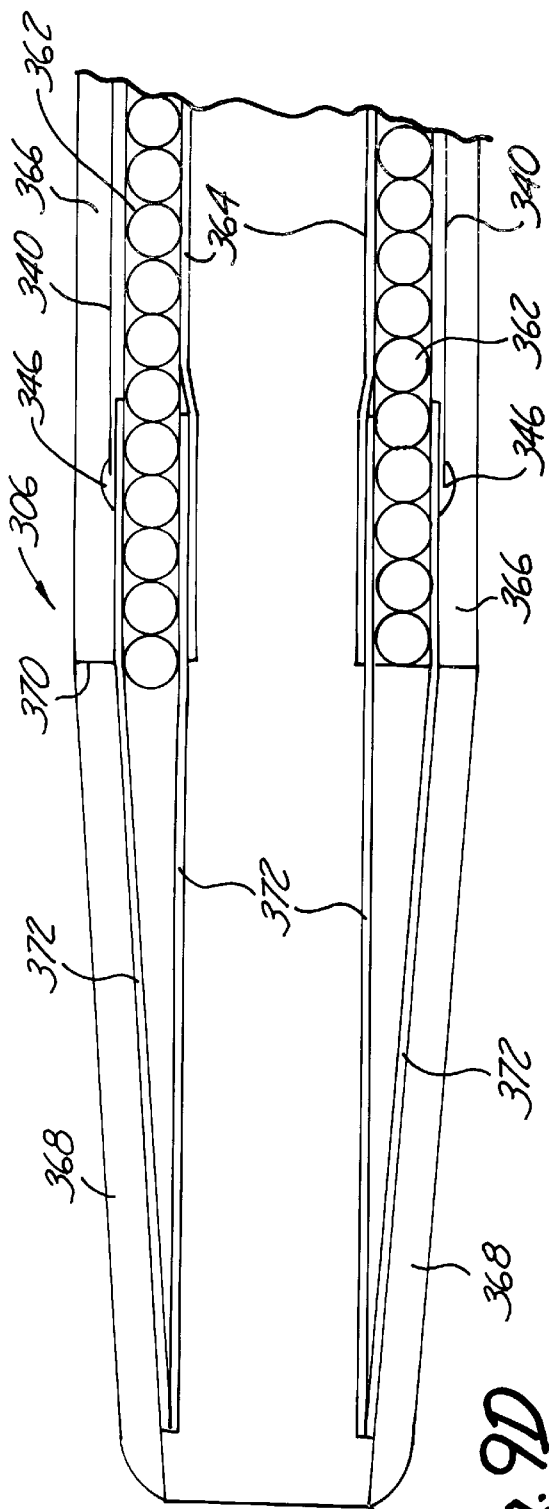
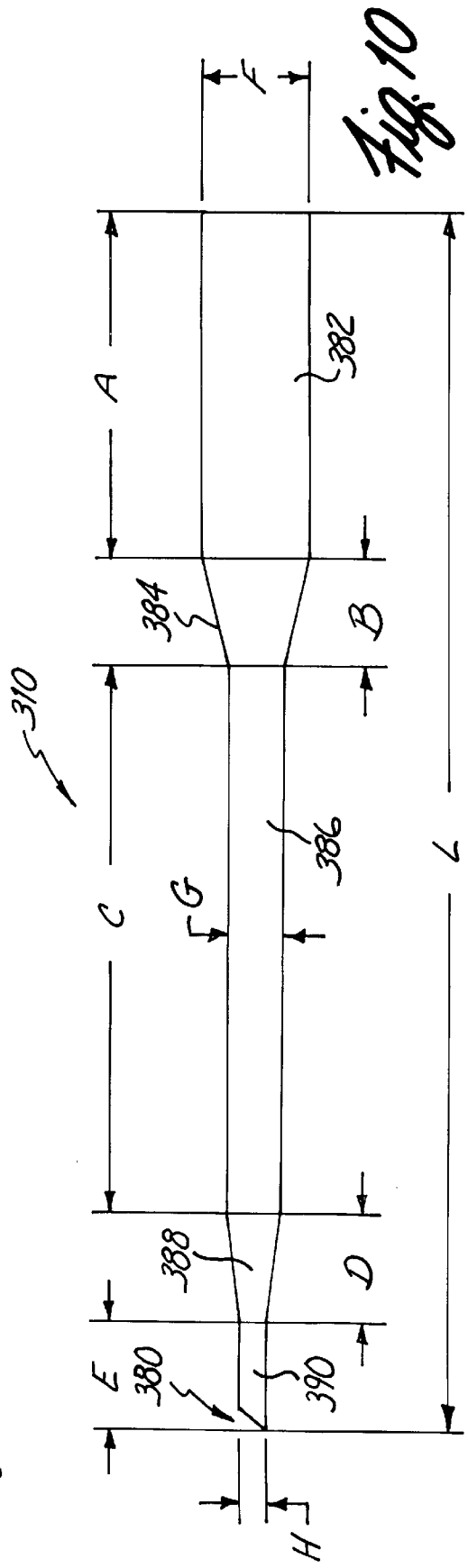
Fig. 9D
Fig. 10

PERCUTANEOUS BYPASS APPARATUS AND METHOD

CROSS-REFERENCE TO RELATED APPLICATION

The present application is related to copending patent application Ser. No. 09/088,496 entitled PERCUTANEOUS CORONARY ARTERY BYPASS THROUGH A VENOUS VESSEL, the disclosure of which is hereby fully incorporated by reference.

BACKGROUND OF THE INVENTION

The present invention generally relates to minimally invasive surgery. In particular, the present invention relates to percutaneous translumenal minimally invasive coronary surgery.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenosis include balloon angioplasty and pharmacological treatment. However, where the occlusion is quite hard, it can be quite difficult, if not impossible, to cross the occlusion with an angioplasty device. In addition, some coronary stenosis are too diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Further, open heart surgery requires quite a lengthy recovery period which involves an increased hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

Given the difficulties of the techniques discussed above, another approach has been developed which does not require stoppage of the heart or an open chest during execution. This approach is to perform a bypass using a minimally invasive technique by entering the upper chest cavity, through a hole between ribs under visual observation. Such a technique is often referred to as minimally invasive direct coronary artery bypass (MIDCAB) (where the heart is not stopped), or heart port (where the heart is stopped). Such a system which is used to perform a bypass is disclosed in the Sterman et al. U.S. Pat. No. 5,452,733.

Yet another approach has been developed which does not require stoppage of the heart or an open chest. This alternative approach is even less invasive than the MIDCAB approach because it does not require accessing the upper chest cavity through a hole between the ribs.

In particular, this alternative approach, which may be referred to as percutaneous translumenal minimally invasive coronary surgery, involves accessing the coronary vasculature from within the vasculature of the body. For example, a percutaneous translumenal approach may involve accessing the femoral artery in the groin region and advancing a suitable device to the coronary arteries by way of the aorta. Once in the coronary vasculature, the restriction may be bypassed by exiting the coronary artery proximal of the restriction and defining an alternative fluid path to the coronary artery distal of the restriction. An example of this approach is disclosed in International Application No. PCT/US96/16483.

SUMMARY OF THE INVENTION

The present invention provides several devices and methods for performing percutaneous translumenal minimally invasive coronary surgery, particularly bypass surgery. Specifically, the present invention permits a physician to perform percutaneous bypass surgery involving one or more of the following basic steps: determining a proper location for treatment, navigating a suitable catheter to the treatment site, creating an extravascular opening and pathway, monitoring the progress of creating the opening and pathway, and maintaining the extravascular opening and pathway. One or more extravascular openings and/or pathways may be created to define a fluid path or bypass around the vascular restriction. Several devices and methods are included in the present invention for performing one or more of these steps. Those skilled in the art will recognize that the devices of the present invention may be modified (e.g., combined or separated) to perform singular functions or multiple functions without departing from the scope and spirit of the present invention.

The extravascular opening may be any or a combination of the following: an arterial entry or reentry, an arterial exit, a venous entry or re-entry, and/or a venous exit. The pathway may be established external to the heart muscle (e.g., the pericardial space), internal to the heart muscle (e.g., the myocardium), and/or in the case of adjacent vessels, the pathway may be defined by the openings in the vascular wall(s).

One embodiment of the present invention provides an intravascular catheter for creating an extravascular opening in a vessel wall. The catheter includes an elongate shaft adapted for intravascular navigation, an anchoring mechanism disposed on the distal end of the shaft, and a tissue penetrating member having a proximal end slidably disposed in the shaft of the catheter and a distal end including a tissue penetrating mechanism. The tissue penetrating member is extendable between a retracted position and penetrating position wherein the tissue penetrating mechanism extends completely through the vessel wall to establish an extravascular opening therethrough. The catheter may include a stiffening member slidably disposed about the tissue penetrating member for providing rigidity to the distal portion.

The anchoring mechanism may comprise, for example, an inflatable balloon that is deflated in the delivery position and inflated in the anchoring position. The distal end of the tissue penetrating member may exit the shaft proximal or distal of the anchoring mechanism, or the tissue penetrating member may exit the anchoring mechanism.

Another embodiment of the present invention provides a method of bypassing a restriction in a vessel using an intravascular catheter having a tissue penetrating member. The method involves initially retracting the tissue penetrating member into the catheter such that the tissue penetrating mechanism is retracted inside the catheter (this may be done by the treating physician or by the manufacturer of the catheter). The catheter is then translumenally navigated to the treatment site, preferably to a position adjacent the restriction, typically an arterial restriction. The tissue penetrating member is then actuated such that it penetrates completely through the wall of the vessel to establish an extravascular opening. The tissue penetrating member may be further actuated to establish a pathway. The tissue penetrating member is then retracted inside the catheter and the catheter may be withdrawn.

The catheter may include an anchor mechanism that is actuated prior to actuating the tissue penetrating member. Preferably, the anchor mechanism is anchored adjacent the restriction in the vessel. If the anchor mechanism is a balloon, the anchor mechanism may be actuated by inflating the balloon.

The step of creating an extravascular opening and pathway may be monitored by injecting radiopaque contrast media into the penetrating member, observing the penetrating member under fluoroscopy as it penetrates the wall of the vessel, and retracting the penetrating member when contrast media is observed exiting the distal end of the penetrating member into an adjacent vessel.

Alternatively, the step of creating an extravascular opening and pathway may be monitored by emitting light from the distal end of the penetrating member, detecting light reflected by tissue adjacent the distal end of the penetrating member, and retracting the penetrating member when the reflected light indicates that the penetrating member is in a lumen in an adjacent vessel.

A further alternative of monitoring the step of creating an extravascular opening and pathway is by emitting light from the distal end of the penetrating member, detecting light emitted from the distal end of the penetrating member in a lumen of an adjacent vessel, and retracting the penetrating member when the detected light indicates that the penetrating member is in the lumen of the adjacent vessel.

Yet a further alternative of monitoring the step of creating an extravascular opening and pathway is by measuring pressure at the distal end of the penetrating member, observing the pressure as the penetrating member penetrates the wall of the vessel, and retracting the penetrating member when the pressure indicates that the penetrating member is in a lumen of an adjacent vessel.

The step of creating an extravascular opening and pathway may also be monitored utilizing intravascular ultrasound devices and techniques.

The extravascular opening may be modified (e.g., enlarged) to accommodate a means to maintain the opening and pathway, such as a stent or graft. For example, a dilator may be navigated to the opening and used to enlarge the opening. The dilator may be rotated as it enlarges the opening in order to reduce friction.

The extravascular opening and pathway may be maintained by providing a stent or graft and positioning the stent or graft in the opening and pathway. Alternatively, the opening and pathway may be maintained by providing a thermal energy emitter for heat fusing the tissue defining the opening and pathway. If the thermal energy emitter comprises a heatable balloon, the balloon may be inflated and activated so as to heat the tissue surrounding the opening and pathway.

BRIEF DESCRIPTION OF THE DRAWINGS

FIG. 3A is a side view of a tissue penetrating device in accordance with one embodiment of the present invention.

FIGS. 3B–3E are cross-sectional views of the tissue penetrating device illustrated in FIG. 3A.

FIG. 4A is a side view of a distal portion of a tissue penetrating device in accordance with another embodiment of the present invention.

FIGS. 4B and 4C are cross-sectional views of the tissue penetrating device illustrated in FIG. 4A.

FIGS. 4D and 4E are cross-sectional views of an alternative embodiment of the tissue penetrating device illustrated in FIG. 4A.

FIG. 7 is a side view of each of the components comprising the tissue penetrating device shown in FIG. 6.

FIGS. 8A and 8B are side views of a pre-curved tip deflection embodiment of the tissue penetrating device illustrated in FIG. 6.

FIGS. 9A through 9D are side views of actuated tip deflection embodiments of the tissue penetrating device illustrated in FIG. 6.

FIG. 10 is a side view of a tissue penetrating member for use with the tissue penetrating device illustrated in FIG. 6.

FIG. 25F illustrates an alternate embodiment of a tissue penetration guide device.

DETAILED DESCRIPTION OF THE PREFERRED EMBODIMENTS

The following detailed description of the preferred embodiments of the present invention should be read with reference to the drawings which are not necessarily to scale and in which similar elements in different drawings are numbered the same. Although the following detailed description illustrates the preferred embodiments, the disclosure herein is merely exemplary and is not intended to limit the spirit or scope of the present invention.

Description of Bypass Procedure

Figure 1:
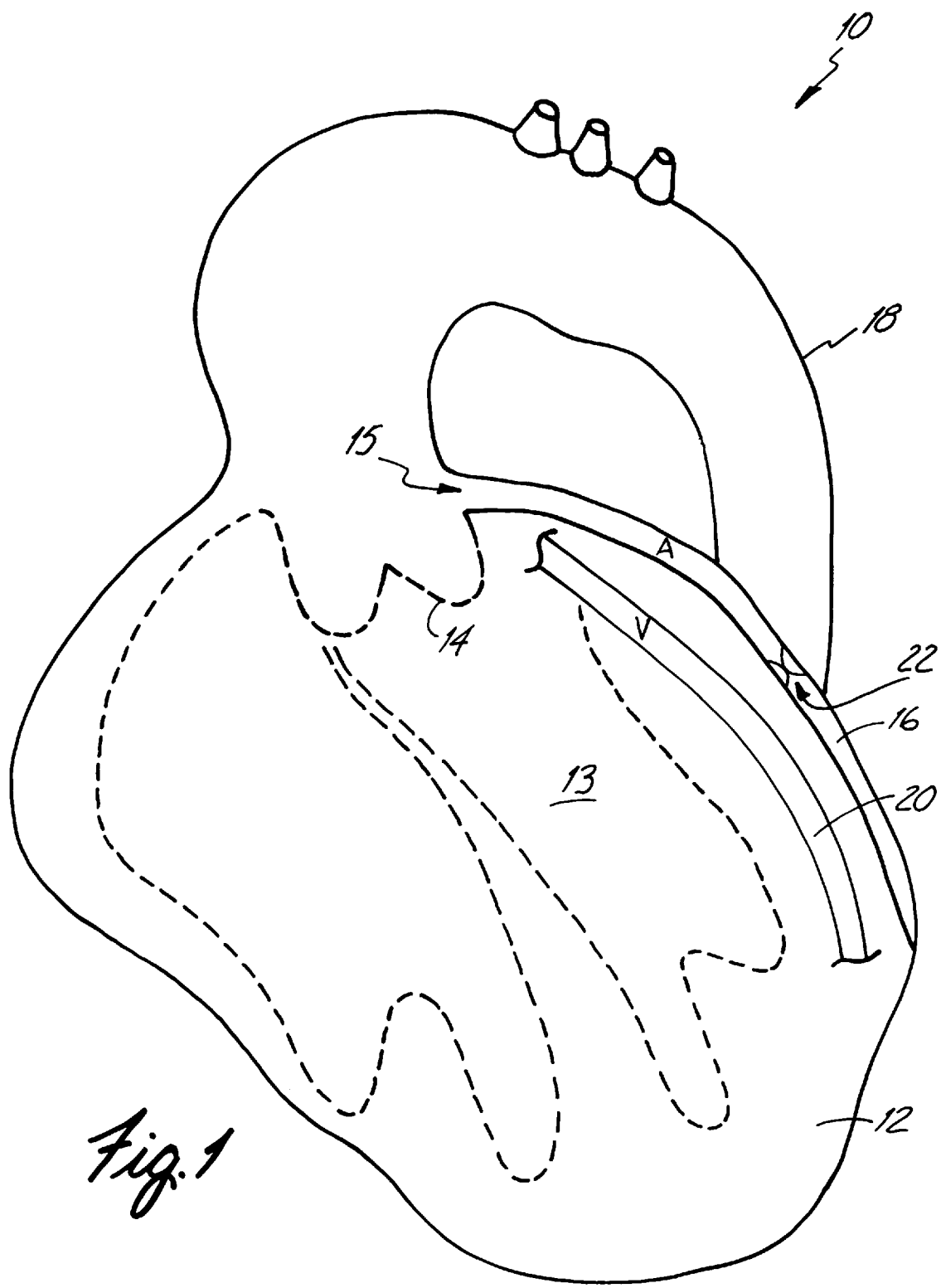
FIG. 1 is a simplified diagram of a human heart illustrating a coronary vein and a coronary artery having a restriction therein.

FIG. 1 is a simplified diagram of a human heart 10 illustrating a coronary vein 20 and a coronary artery 16 having a restriction 22 disposed therein. The human heart 10 includes a heart muscle 12 which causes the left ventricle 13 to pump blood through the valve 14 into the aorta 18. As blood flows from the left ventricle 13 through the valve 14, blood also flows into the coronary artery 16 by way of ostium 15.

Blood flowing in the coronary artery 16 supplies oxygenated blood to the heart muscle 12. As with other muscles in the human body, after the heart muscle 12 uses the oxygenated blood from the coronary artery 16, the expended blood is returned by way of a coronary vein 20. Typically, the coronary arteries 16 are disposed adjacent the coronary veins 20. If a restriction 22 develops in the coronary artery 16, the delivery of oxygenated blood to the heart muscle 12 is significantly compromised if not eliminated. Accordingly, it is desirable to establish an alternative pathway for the oxygenated blood to flow to the heart muscle 12.

Figure 2:
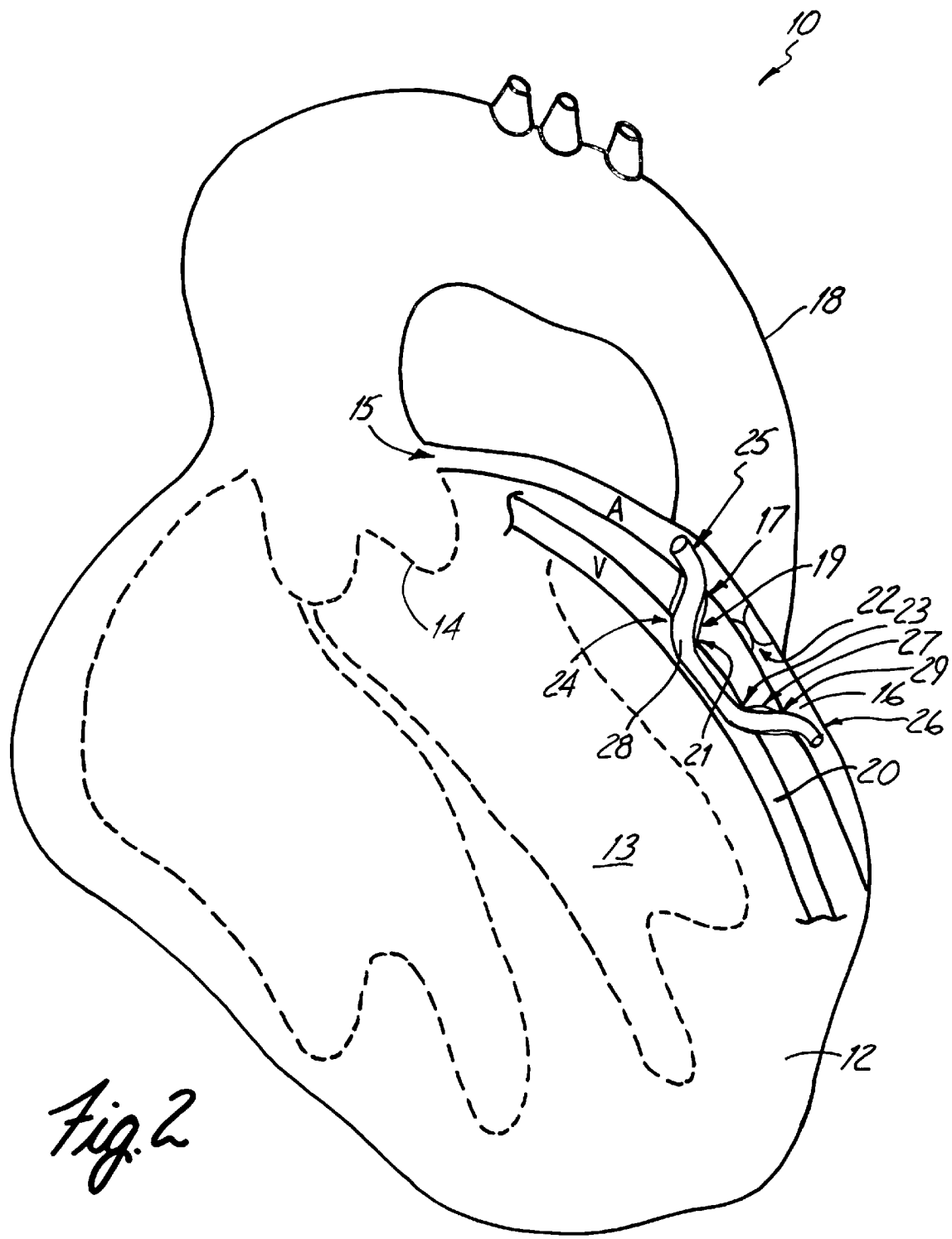
FIG. 2 is a simplified diagram of a human heart illustrating a venous bypass of a restriction.

With reference to FIG. 2, an alternative path is provided by conduit 24, which may be in the form of a vascular graft or the like. The conduit 24 includes a proximal end 25, a distal end 26 and a lumen 28 extending therethrough. The conduit 28 passes through arterial exit hole 17 through passageway 19 into venous entry hole 21 through a portion of the coronary vein 20, into venous exit hole 23 through passageway 27 out arterial re-entry hole 29 and back into the coronary artery 16. With this arrangement, blood flowing into the coronary artery 16 from the ostium 15 flows into the proximal end 25 of the conduit 24, through the lumen 28 and exits the distal end 26 of the conduit 24 thus delivering oxygenated blood to the heart muscle 12. In effect, the conduit 24 provides an alternative path for the oxygenated blood to flow around the restriction 22. A detailed description of this technique is disclosed in International Application No. PCT/US96/16483 which is hereby incorporated by reference.

Although the general method of bypassing a restriction in an artery by providing a conduit via an adjacent vein is known, practical devices and methods have not been previously described to effectively enable this technique by a percutaneous transluminal approach. The percutaneous transluminal technique is particularly difficult from a device standpoint due to the long distance between the vascular access site and the treatment site, the relatively small lumen size of the vascular path, and the precise control required for the technique in a dynamic environment (i.e., a beating heart).

Two primary challenges exist with regard to device design in this percutaneous transluminal technique. Specifically, a suitable device must enable the treating physician to determine the proper location for treatment, navigate to the treatment site, create an extravascular opening and pathway, monitor the progress of creating the opening and pathway, and provide a means to maintain the extravascular opening and pathway. The device must be able to create one or more extravascular openings and/or pathways in order to bypass the restriction.

As used herein, an extravascular opening may comprise any one or a combination of the following: an arterial entry or re-entry, an arterial exit, a venous entry or re-entry, and/or a venous exit. In a similar manner, the term "pathway" as used herein includes, without limitation, the pathway established external to the heart muscle (e.g., a pericardial space), internal to the heart muscle (e.g., the myocardium), and/or in the case of adjacent vessels, the pathway may be defined by the openings in the vascular wall(s).

With reference to FIG. 2, a generic percutaneous translumenal bypass procedure may be described as follows. First, a suitable device is navigated to the coronary vasculature by known means. For example, access to the coronary vasculature may be established by way of the femoral artery and aorta using an access sheath and guide catheter navigated to the coronary ostium using a guidewire. Once the desired device is navigated to the treatment site proximal of the restriction 22 in the coronary artery 16, the treating physician determines the correct penetration site to create an extravascular opening. A tissue penetrating device then creates the extravascular opening in the vascular wall of the artery 16 and may be further used to define a pathway to the coronary vein 20. The progress of creating the extravascular opening and the pathway should be monitored to ensure that a proper position for the extravascular opening and pathway are established.

Once the extravascular opening in the coronary artery 16 is established and a pathway to the coronary vein 20 is defined, an extravascular opening is then established in the coronary vein 20. This may be accomplished utilizing the same tissue penetrating device. The creation of the extravascular opening in the vein 20 should also be monitored to ensure that a proper venous access opening has been established. After creating an opening in the coronary artery 16 and a pathway to an opening in the coronary vein 20, the openings and pathway should be maintained by a suitable means such as a vascular graft or stent or by cauterization. This establishes fluid communication between the coronary artery 16 proximal of the restriction 22 to the coronary vein 20.

The next steps involve establishing a fluid path between the coronary vein 20 and the coronary artery 16 distal of the restriction 22. This may be accomplished in the same manner as described previously, namely, creating an extravascular opening in the coronary vein 20, defining a pathway to the coronary artery 16, creating an extravascular opening in the coronary artery 16 distal of the restriction 22, monitoring the progress of creating the extravascular openings and pathway, and providing a means to maintain the fluid path established.

The devices and methods of use disclosed herein may be used to perform one or more of the above-identified generic functions. In addition, the devices and methods of use disclosed herein may be utilized to perform more specific functions associated with this technique. Those skilled in the art will recognize that several of the devices of the present invention may be combined into a single multi-functional device, or separated into several single-functional devices. Those skilled in the art will recognize that many of the devices of the present invention may be utilized in other minimally invasive bypass techniques not specifically described herein.

Tissue Penetrating Device

FIGS. 3A–3E illustrate a tissue penetrating device 30 which may be used to create an extravascular opening and pathway as described previously. The tissue penetrating device 30 includes a shaft 32 having a manifold 34 connected to its proximal end. Manifold 34 includes an inflation port 36 for inflating the balloon 38 mounted to the distal end of the shaft 32. The catheter 30 is preferably a single operator exchange (SOE) type catheter suitable for easy advancement and exchange over a conventional guidewire 40.

Elongated shaft 32 includes an outer tube 42 which may be formed of a polyimide encased stainless steel braid. The elongated shaft also includes an inflation tube 44 preferably formed of polyimide. The inflation tube 44 provides fluid communication between the inflation port 36 on the manifold 34 and the interior of the balloon 38 to facilitate the inflation and deflation of the balloon 38.

Elongated shaft 32 also houses at least partially along its length a tissue penetrating member 46 and a stiffening member 48. The tissue penetrating member 46 may be, for example, an elongated stainless steel wire having a sharpened distal end. Alternatively, the tissue penetrating member 46 may comprise any suitable structure that is capable of penetrating vascular and muscular tissue by mechanical, thermal, or other suitable means. The tissue penetrating member 46 and the stiffening member 48 are illustrated exiting the elongated shaft 32 proximal of the balloon 38. It is also contemplated that the tissue penetrating member 46 and the stiffening member 48 may exit the catheter 30 at any location adjacent the balloon 38.

The distal portion of the shaft 32 includes a guidewire tube 50 which contains the guidewire 40 therein. The guidewire tube 50 extends from the distal end of the catheter 30 to a point proximal of the distal end of the catheter 30 and distal of the proximal end of the catheter 30. Preferably, the guidewire tube 50 is of a length suitable to facilitate single operator exchange (SOE) of the catheter 30 over a conventional length guidewire 40. The guidewire tube 50, which may be formed of any suitable material, is connected to the outer tube 42 by shrink wrap tube 52. The distal end of the elongated shaft 32 is connected to the proximal waist 54 of the balloon 38 by known means.

The proximal end of the stiffening member 48 is connected to slide 56 and the proximal end of the tissue penetrating member 46 is connected to slide 58. Both the tissue penetrating member 46 and the stiffening member 48 pass through hub 60 which is rigidly connected to the elongate shaft 32. With this arrangement, the stiffening member 48, which is preferably formed of a super elastic hypotube such as Nitinol, may be advanced or retracted by moving slide 56 relative to hub 60. In a similar manner, the tissue penetrating member 46 may be advanced or retracted by actuating the slide 58 relative to the hub 60. The tissue penetrating member 46 and the stiffening element 48 are guided by and slidable within the hub 60 and the elongate shaft 32.

In use, the catheter 30 is navigated through the vascular system until the balloon 38 is disposed adjacent to the treatment site. Specifically, the balloon 38 is preferably positioned immediately proximal of the restriction 22 in the coronary artery 16. Preferably, the catheter 30 is navigated to the treatment site with the balloon 38 in a deflated state. When the balloon 38 is in the desired position, it is inflated to anchor the distal end of the catheter 30 at the treatment site. The balloon 38 essentially anchors the distal end of the catheter 30 adjacent the treatment site such that the tissue penetrating member 46 moves in concert with the coronary artery 16. This maintains the position of the tissue penetrating member 46 while the extravascular opening and pathway are being created. If the position of the tissue penetrating member 46 were not maintained during the formation of the extravascular opening and pathway, the tissue penetrating member would move relative to the coronary artery 16, potentially causing the formation of an extravascular opening in an undesired location and may even cause damage to the surrounding heart tissue.

Although a balloon 38 is illustrated as a means to anchor the distal end of the catheter 30, it is contemplated that other mechanisms may be employed. For example, an expandable braid or bristle structure may be utilized to engage the interior surface of the coronary artery 16. Those skill in the art will recognize that these and other mechanisms may be employed in place of balloon 38 to provide the desired anchoring effect.

With the anchoring balloon 38 inflated, an extravascular opening and pathway may be created by advancing the tissue penetrating member 46. If the column strength of the tissue penetrating member 46 is insufficient to advance it through the vascular tissue and/or other heart tissue, the stiffening member 48 may be advanced along the tissue penetrating member 46 to provide additional backup support. Conversely, if additional flexibility is required along the length of the tissue penetrating member 46, the stiffening member 48 may be retracted along the tissue penetrating member 46 to provide additional flexibility. In this manner, the flexibility or stiffness of the tissue penetrating member may be varied along its length depending on tissue and anatomical characteristics encountered.

The exit port 62 of the tissue penetrating member 46 and the stiffening member 48 is preferably at an angle with the longitudinal axis of the shaft 32. Specifically, the exit port 62 is preferably at a 30° to 40° angle with the longitudinal axis of the catheter 30, although it can be at a 0–70° angle with respect to the longitudinal axis of the catheters 30 depending on the desired direction of tissue penetration. Furthermore, the distal end of the tissue penetrating member 46 and/or the stiffening member 48 may be angled or curved to facilitate steering of the tissue penetrating member 46.

FIG. 4A is a side view of a distal portion of a tissue penetrating device 70 in accordance with another embodiment of the present invention. FIGS. 4B and 4C illustrate cross-sectional views of the tissue penetrating device 70 taken along lines A—A and B—B respectively. FIGS. 4D and 4E illustrate cross-sectional views of an alternative embodiment of the tissue penetrating device 70 taken along lines A—A and B—B respectively. Tissue penetrating device 70 is substantially similar to tissue penetrating device 30 except as described herein.

In the first embodiment of the tissue penetrating device 70 as illustrated in FIGS. 4A, 4B and 4C, the distal end of the elongate shaft 72 is connected to an eccentric balloon 74. The elongate shaft 72 includes an outer tube 76 which houses a guidewire tube 50 having a guidewire 40 disposed therein. Outer tube 76 includes an inflation lumen 77 in fluid communication with interior of the balloon 74. The outer tube 76 also houses the tissue penetrating member 46 disposed in the stiffening member 48 which, in turn, is disposed in a puncture tube 78.

In this illustrative embodiment, the puncture tube 78 terminates at exit port 80. Exit port 80 may be disposed at any point along the length of the balloon 74, preferably eccentrically located at the perimeter of the balloon 74. With this arrangement, the tissue penetrating member 46 is immediately adjacent the interior surface of the coronary artery 16 upon inflation of the balloon 74. This provides additional backup support to the tissue penetrating member 46 as it is advanced through the vascular wall and other heart tissues. It is contemplated, accordingly, that the stiffening member 48 may be eliminated given the same backup effect of the puncture tube 78 rigidly connected to the balloon 74.

In the second embodiment of the tissue penetrating device 70 illustrated in FIGS. 4A, 4D and 4E, the elongate shaft 72 is a multi-lumen tube 82 defining an inflation lumen 84 and a puncture lumen 86. The inflation lumen 84 is in fluid communicating with interior of the balloon 74 by way of inflation ports 88. The multi-lumen tube 82 is similar to the outer tube 76 illustrated in FIG. 4B except that the need for a separate puncture tube 78 is eliminated by providing septum 83. All other aspects are essentially the same.

Although the tissue penetrating device 70 is illustrated in FIGS. 4A–4E as a conventional over the wire (OTW) type catheter requiring a guidewire port in the manifold, it is contemplated that the tissue penetrating device 70 may be a SOE type catheter as illustrated in FIG. 3A.

FIGS. 5A–5F illustrate various configurations of a distal portion of a tissue penetrating device disposed in the coronary vasculature. Specifically, the various embodiments illustrated in FIGS. 5A–5F illustrate how the tissue penetrating member 46 may be positioned to penetrate the tissue at different points along the length of the device. Those skilled in the art will recognize that the various embodiments illustrated in FIGS. 5A–5F may be adapted to catheters 30 and 70 illustrated in FIGS. 3A and 4A respectively.

Figure 5A:
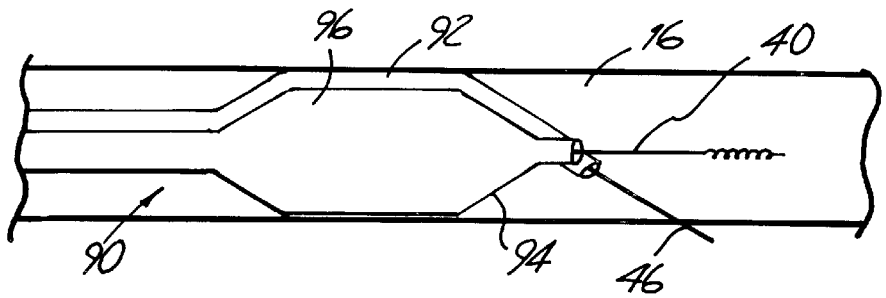
FIG. 5A is a side view of a distal portion of a tissue penetrating device disposed in the coronary vasculature in accordance with another embodiment of the present invention.

Tissue penetrating device 90 illustrated in FIG. 5A illustrates the tissue penetrating member 46 exiting a puncture tube 92 adjacent the distal cone 94 of the inflatable balloon 96. The angle at which the tissue penetrating member 46 exits the puncture tube 92 is dictated by the geometry of the distal balloon cone 94.

Figure 5B:
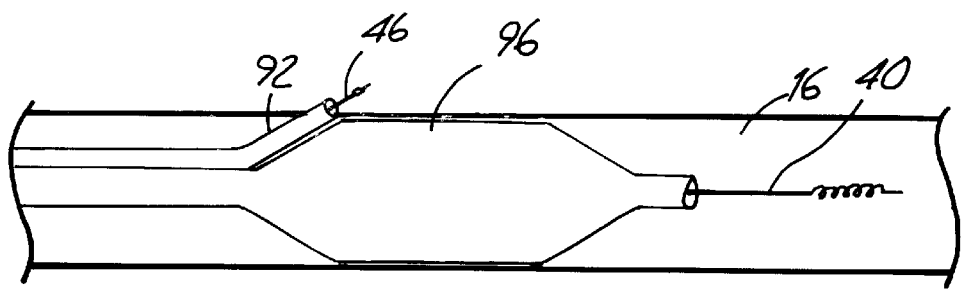
FIG. 5B is a side view of a distal portion of a tissue penetrating device disposed in the coronary vasculature in accordance with another embodiment of the present invention.

In a similar manner, the tissue penetrating device 100 illustrated in FIG. 5B includes a puncture tube 92 which terminates along the proximal cone 93 of the balloon 96. In this embodiment, the angle at which the penetrating member 46 exits the puncture tube 92 is dictated by the geometry of the proximal cone 93.

Figure 5C:
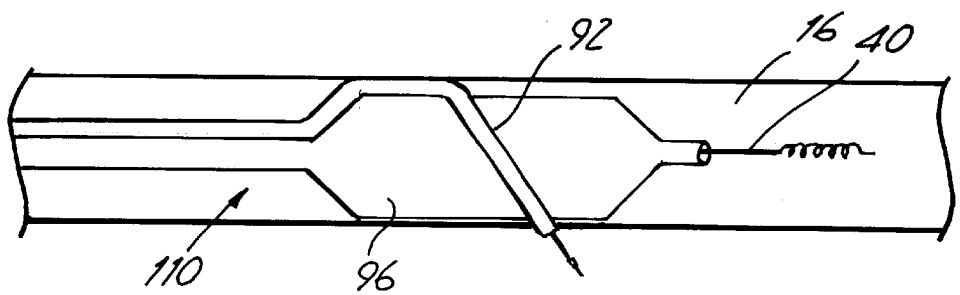
FIG. 5C is a side view of a distal portion of a tissue penetrating device disposed in the coronary vasculature in accordance with another embodiment of the present invention.

The tissue penetrating device 110 illustrated in FIG. 5C includes a puncture tube 92 wrapped around the perimeter of the balloon 96. The angle at which the penetrating member 46 enters the surrounding tissue is dictated by the angle at which the puncture tube 92 is secured to the balloon 96.

Figure 5D:
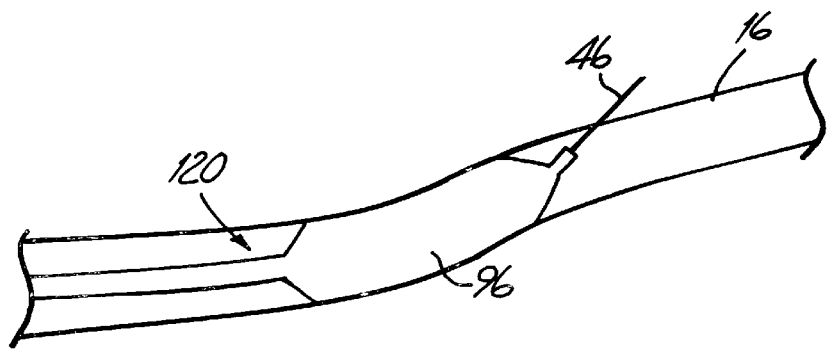
FIG. 5D is a side view of a distal portion of a tissue penetrating device disposed in the coronary vasculature in accordance with another embodiment of the present invention.

The tissue penetrating device 120 shown in FIG. 5D illustrates the tissue penetrating member 46 disposed in the guidewire lumen in place of the guidewire. In this embodiment, the balloon 96 is preferably curved such that the tissue penetrating member 46 penetrates the surrounding tissue at an angle dictated by the curvature of the balloon 96. Alternatively, the balloon 96 may be of a flexible nature such that the balloon conforms to curved vasculature and the angle at which the penetrating member 46 enters the surrounding tissue is dictated by the curvature of the vasculature.

Figure 5E:
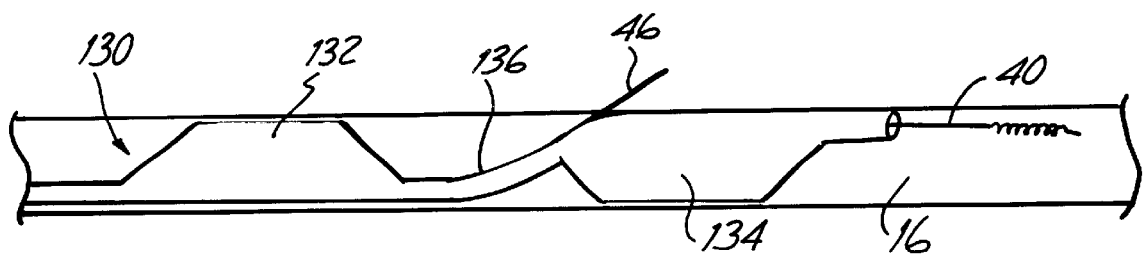
FIG. 5E is a side view of a distal portion of a tissue penetrating device disposed in the coronary vasculature in accordance with another embodiment of the present invention.

The tissue penetrating device 130 illustrated in FIG. 5E includes a proximal balloon 132 and distal balloon 134. An intermediate shaft 136 is disposed between the proximal balloon 132 and the distal balloon 134. The tissue penetrating member 46 exits the intermediate shaft 136 adjacent the proximal end of the distal balloon 134. The intermediate shaft 136 is eccentrically connected to the distal end of the proximal balloon 132 and eccentrically connected to the proximal end of the distal balloon 134 such that the axis of the intermediate shaft 136 is at an angle with the longitudinal axis of the distal portion of the catheter 130. The angle at which the penetrating member 46 penetrates the surrounding tissue is dictated by the angle of the intermediate shaft 136.

Figure 5F:
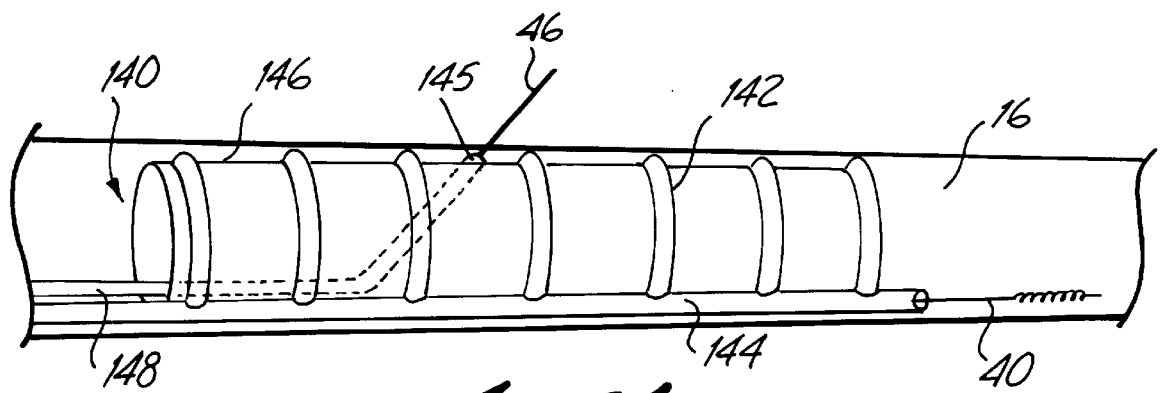
FIG. 5F is a side view of a distal portion of a tissue penetrating device disposed in the coronary vasculature in accordance with another embodiment of the present invention.

The tissue penetrating device 140 illustrated in FIG. 5F includes a helical balloon 142 connected to the distal end of the elongate shaft 144. An inner sheath 146 is connected to the interior portion of the helical balloon 142 to define a space between the sheath 146 and the inside surface of the coronary artery 16. The puncture tube 148 extends along the proximal portion of the shaft 144 and is connected to the sheath 146 at a point 145 laterally displaced from the distal end of the elongate shaft 144. The angle at which the tissue penetrating member 46 penetrates the surrounding tissue is dictated by the angle of the distal end of the puncture tube 148.

Figure 6:
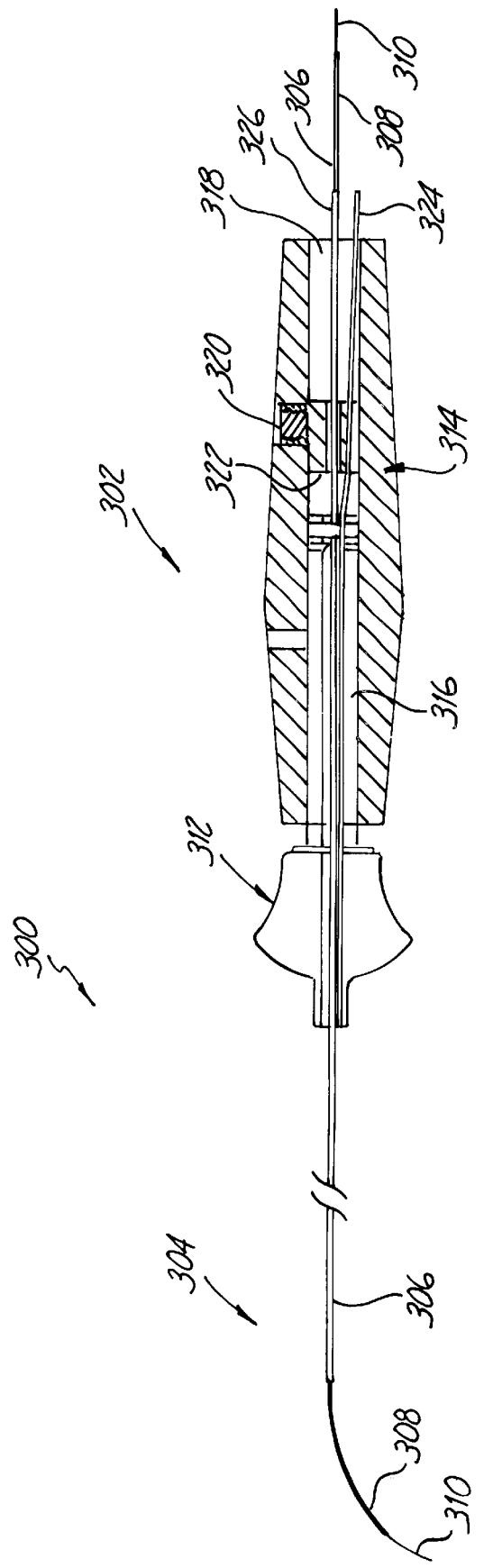
FIG. 6 is a partially cross-sectioned side view of a tissue penetrating device in accordance with another embodiment of the present invention.

FIG. 6 is a partially cross-sectioned side view of a tissue penetrating device 300 in accordance with another embodiment of the present invention. Tissue penetrating device 300 includes an actuation assembly 302 connected to a shaft assembly 304. The shaft assembly 304 includes a penetrating member 310 disposed in a stiffening member 308 which in turn is disposed in an outer tube 306. The outer tube 306 is preferably formed of a polymer encased stainless steel braid. Stiffening tube 308 is preferably formed of a super elastic metal such as Nitinol incorporating a series of lateral slots or grooves at the distal end thereof to impart flexibility. Tissue penetrating member 310 is also preferably formed of a super elastic metal such as Nitinol, but may also be formed of stainless steel or a suitable polymer. The tissue penetrating member 310 is slidably disposed in the stiffening member 308 and may be removed from the stiffening member 308 to accommodate a conventional guide wire. Similarly, the stiffening tube 308 is slidably disposed in the outer tube 306.

The actuation assembly 302 includes actuator 312 and handle 314. The actuator 312 includes a neck portion 316 disposed in a bore 318 of the handle 314. The neck 316 of the actuator 312 is slidably disposed in the bore 318 of the handle 314. The actuator assembly 302 also includes a set screw 320 which engages a compression fitting 322 for releasably securing the shaft assembly 304 relative to the handle 314. The actuator assembly 302 further includes an auxiliary tube 324 to facilitate the insertion of auxiliary devices such as a guide wire, a balloon catheter, etc.

The actuator 312 moves relative to the handle 314 to cause the tip of the shaft assembly 304 to deflect. The actuator 312 may be connected to one or more pull wires connected to the distal end of the penetrating member 310 or the stiffening tube 308. With this arrangement, longitudinal movement of the actuator 312 relative to the handle 314 causes the tip of either the penetrating member 310 or the stiffening tube 308 to deflect. Examples of such tip deflection mechanisms are illustrated in FIGS. 9A through 9D.

Alternatively, the actuator 312 may be connected to pull wires which are connected to the stiffening member 308 or the outer tube 306 or both. With this arrangement, longitudinal movement of the actuator 312 relative to the handle 314 causes corresponding longitudinal movement of the stiffening tube 308 relative to the penetrating member 310, or causes longitudinal movement of the outer tube 306 relative to the stiffening tube 308, depending on which member 306 or 308 the pull wires are connected to. An example of this arrangement is illustrated in FIGS. 8A and 8B.

If the pull wires are connected to the stiffening tube 308, a curve may be pre-formed in the distal portion of the penetrating member 310 such that when the stiffening tube 308 is retracted, the distal portion of the tissue penetrating member 310 assumes its pre-formed curve. Conversely, when the stiffening tube 308 is advanced relative to the penetrating member 310, the relative stiffness of the stiffening tube 308 causes the penetrating member 310 to assume a substantially linear shape or other shape as defined by the stiffening tube 308.

Similarly, if the pull wires are connected to the outer tube 306, the stiffening tube 308 preferably includes a pre-formed curve such that when the outer tube 306 is retracted, the stiffening tube 308 assumes its pre-formed shape. Conversely, when the outer tube 306 is advanced over the stiffening tube 308, the distal portion of the stiffening tube 308 assumes a substantially linear shape or other shape as defined by the outer tube 306.

FIG. 7 is a side view of each of the main components comprising the actuator assembly 302 and the shaft assembly 304 of the tissue penetrating device 300 as illustrated in FIG. 6. The penetrating member 310 is slidably disposed in the stiffening tube 308 which in turn is slidably disposed in the outer tube 306. The outer tube 306 is slidably disposed in a handle tube 326 which in turn is disposed in the actuator 312. The actuator 312 is slidably disposed in the handle 314. To accommodate this co-axial arrangement, the stiffening tube 308, the outer tube 306, the handle tube 326, the actuator 312 and the handle 314 each include a lumen or bore extending therethrough.

The actuator assembly 302 also includes a short tube 328 for connection to one or more pull wires (not shown). The short tube 328, preferably a stainless steel hypotube, is slidably disposed on the stiffening tube 308 and slidably disposed in the outer tube 306. The short tube 328 is aligned with a slot 330 in the outer tube, a slot 332 in the handle tube 326 and a slot 334 in the neck portion 316. With this arrangement, the pull wires connected to the short tube 328 may pass through the grooves or slots 330, 332 and 334 for connection to the actuator 312 in recess 336. Accordingly, longitudinal movement of the actuator 312 causes corresponding longitudinal movement of the short tube 328 by way of the pull wires passing through the slots 330, 332, 334.

As stated previously, the actuator assembly 302 may be used to deflect the tip of the stiffening tube 308 or the outer tube 306. Alternatively, the actuator assembly 302 may be used to retract the stiffening tube 308 relative to the penetrating member 310 or retract the outer tube 306 relative to the stiffening tube 308 to expose a pre-formed curve in either the penetrating member 310 or the stiffening tube 308 respectively.

If the actuator assembly 302 is utilized to cause the tip of either the penetrating member 310 or the stiffening tube 308 to deflect, the short tube 328 is connected to a second set of one or more pull wires extending along the length of the shaft assembly 304. The distal ends of the second set of pull wires (not shown) are connected to the distal end of the stiffening tube 308 or the outer tube 306, depending on which is to be deflected. If the actuator assembly 302 is used to retract either the stiffening tube 308 or the outer tube 306, the short tube 328 is rigidly connected to either the stiffening tube 308 or the outer tube 306, depending on which is to be retracted.

In each of these embodiments, the tissue penetrating member 310 may be manually actuated to either advance or retract within the stiffening tube 308. As illustrated in FIGS. 6 and 7, the set screw 320 engages the compression fitting 322 which in turn engages the handle tube 326. With this arrangement, the handle tube 326 remains stationary relative to the handle 314. Depending on which tube 306 or 308 is to remain stationery during actuation, the handle tube 326 may be rigidly connected to the stationary tube.

FIGS. 8A and 8B illustrate side views of a pre-formed curve embodiment of the shaft assembly 304 of the tissue penetrating device 300 illustrated in FIG. 6. FIG. 8A illustrates the stiffening tube 308 in the retracted position leaving the distal end of the penetrating member 310 exposed. In the exposed condition, the distal end of the tissue penetrating member 310 assumes its pre-formed curve. With this arrangement, the shaft assembly 304 or simply the tissue penetrating member 310 may be rotated to steer the distal end of the tissue penetrating member 310 in the desired direction for tissue penetration. FIG. 8B illustrates the stiffening tube 308 advanced over the distal portion of the tissue penetrating member 310 such that the pre-formed curve in the tissue penetrating member 310 is straightened by the relatively stiff distal end of the tube 308. In this condition, the shaft assembly 304 may be navigated through the vasculature with the tissue penetrating member 310 protected to avoid penetration at an undesired location.

FIGS. 9A through 9D are side views of tip deflection embodiments of the shaft assembly 304 of the tissue penetrating device 300 illustrated in FIG. 6. In each of the embodiments illustrated in FIG. 9A through 9C, the pull wire 340 extends along the shaft assembly 304 in the annular space between the outer tube 306 and the stiffening tube 308. The proximal end of the pull wire 340 is connected to the short tube 328 as illustrated in FIG. 7. The stiffening tube 308 includes a pattern of lateral slots or grooves to impart flexibility along its length.

FIG. 9A illustrates a tip deflection embodiment wherein a pull wire 340 is connected to a collar 342. The collar 342 is rigidly connected to the distal end of the stiffening tube 308 such that longitudinal movement of the wire 340 causes the distal end of the tube 308 to deflect about pivot point 344. Pivot point 344 may be predefined by a relatively flexible section of the tube 308 or may be inherently present by virtue of the relatively stiff collar 342 and the relatively stiff outer tube 306. The wire 340 may be stainless steel, super elastic metal such as Nitinol, a polymer fiber or other suitable material. The collar 342 may be formed of a stainless steel tube, a super elastic metal tube, or other suitable material. The wire 340 may be connected to the collar 342 by a suitable joint 346 such as solder or braze.

FIG. 9B illustrates a tip deflection embodiment utilizing a hinge 350. Hinge 350 includes a proximal collar 352 and a distal collar 354. The pull wire 340 is connected to the distal collar 354 at joint 346. With this arrangement, the distal end of the stiffening tube 308 is deflected about pivot point 356 by longitudinal movement of the wire 340.

FIGS. 9C (1) and 9C (2) illustrate side views of yet another tip deflection embodiment of the shaft assembly 304 of the tissue penetrating device 300 illustrated in FIG. 6. In this embodiment, the outer tube 306 includes a window 360 through which the distal end of the stiffening tube 308 may be deflected. Providing the window 360 deflection enables the distal portion of the tissue penetration member to be isolated from the surrounding tissue and further enables the distal end of the stiffening tube 308 to be deflected in a precise direction defined by the window 360. As with the embodiment illustrated in FIG. 9A, the embodiment illustrated in FIGS. 9C (1) and 9C (2) employ a collar 342 rigidly connected to the pull wire 340 at a connection 346. Longitudinal movement of the pull wire 340 causes the distal end of the stiffening tube 308 to deflect about pivot point 344 and out window 360.

FIG. 9D illustrates a side view of another tip deflection embodiment of the shaft assembly 304 of the tissue penetrating device 300 illustrated in FIG. 6. In this embodiment, the distal end of the outer tube 306 is deflected, as opposed to the distal end of the stiffening tube 308 illustrated in FIGS. 9A through 9C. Outer tube 306 includes a helical coil 362 extending along its length to impart flexibility and torquability. Outer tube 306 further includes an inner layer 364 preferably formed of a low friction polymer such as PTFE. The outer tube 306 further includes an outer layer 366 formed of a suitable flexible polymer. The distal section of the outer tube 306 is formed of a softer tip material 368. The tip material 368 is preferably a low durometer polymer relative to the outer layer 366. The tip 368 may be heat fused to the outer layer 366 at joint 370 using conventional techniques. The distal end of the outer tube 306 further includes a pair of opposing ribbons 372, preferably formed of rectangular stainless steel wire. The ribbon 372 imparts directional flexibility to the distal end of the tube 306. The pull wire 340 is connected to the ribbon 372 at joint 346. In this illustrative embodiment, two pull wires 340 are shown for actuation in opposing directions.

As with all embodiments illustrated in FIGS. 2 through 10, the tissue penetrating member 46, 310 may be removed to accommodate a guide wire, a fiber optic light guide, or other auxiliary device. For example, once the extravascular opening and pathway are established by the tissue penetrating member 46, 310, the stiffening tube 48, 308 may be advanced therethrough, followed by removal of the tissue penetrating member 46, 310, followed by advancement of the guide wire through the tube 48, 308 to maintain the extravascular opening and pathway. With the guide wire in place, the entire device 30, 70, 90, 100, 110, 120, 130, 140, 300 may be removed leaving the guide wire therein. With the guide wire remaining in place, a deployment device may be advanced over the guide wire for deployment of a suitable conduit 28.

FIG. 10 is a side view of a penetrating member 310 for use with any of the tissue penetration devices 30, 70, 90, 100, 110, 120, 130, 140, and particularly with the tissue penetrating device 300 illustrated in FIG. 6. Tissue penetrating member 310 illustrated in FIG. 10 is particularly useful for transmitting torque along the length of the member 310 in order to steer the distal tip thereof. As with all embodiments of the tissue penetrating member incorporating a mechanical piercing mechanism, the distal tip 380 may be sharpened to facilitate penetration through vascular and muscular tissue.

Tissue penetrating member 310 is preferably formed of a super elastic metal such as Nitinol. The tissue penetrating member 310 may have an overall length L of approximately 48 inches. The tissue penetrating member 310 preferably includes a proximal uniform section 382, a proximal taper 384, a mid-uniform section 386, a distal taper 388 and a distal uniform section 390. The length A of section 382 is preferably approximately 16 inches. The length B of section 384 is preferably 3.0 inches. The length C of section 386 is preferably approximately 24 inches. The length D of section 388 is preferably approximately 3.0 inches. The length E of section 390 is preferably 2.0 inches and may be heat set to impart a pre-formed curve. If a large stiffening tube 308 is utilized, the preferred diameters F, G, H are 0.0468, 0.015, and 0.010 inches, respectively, but are not limited to those preferred diameters. If a small stiffening tube 308 is utilized, the preferred dimensions F, G, H are 0.0384, 0.012, and 0.010 inches, respectively. These dimensions have been found to impart superior torquability and flexibility.

Dilator Devices

Refer now to FIGS. 11A–11D which illustrate side views of a distal portion of various dilator devices in accordance with the present invention. Each of the devices 150, 160, 170 and 180 illustrated in FIGS. 11A–11D may be used to dilate an extravascular opening created by any of the tissue penetrating devices disclosed herein such as device 30 or device 70 illustrated in FIGS. 3A and 4A respectively. The term "dilate" refers to the enlargement of the extravascular opening and/or the pathway. Enlargement of the extravascular opening and/or the pathway may be desirable to accommodate a suitable conduit 28 (as illustrated in FIG. 2) in order to maintain the opening and pathway. The conduit 28 may be delivered by a separate device or may be delivered by the dilator device 150, 160, 170, 180. For purposes of illustration only, each of the dilator devices 150, 160, 170 and 180 is shown carrying a conduit in the form of a stent 210 for delivery by a stent delivery catheter 212. The stent 210 and the stent delivery catheter 212 are merely schematically illustrated and those skilled in the art will readily recognize that a number of stents or grafts and their associated delivery systems may be utilized to provide conduit 28.

Each of the dilator devices 150, 160, 170 and 180 may be rotated as the dilator portion is inserted through the extravascular opening and pathway. Rotating the dilator in a direction indicated by arrow 200, for example, reduces the amount of friction between the dilator device and the tissue being dilated. Specifically, since the coefficient of kinetic friction is typically lower than the coefficient of static friction, the resistive frictional forces acting on the dilator device is also proportionally lower. Rotation of the dilator may be in either direction and may be continuous or cycled. Furthermore, the movement of the dilator may be reciprocated in any given direction (e.g., longitudinal, rotational, etc.) such that the dilator vibrates as it passes through the surrounding tissue. Virtually any motion of the dilator relative to the surrounding tissue causes the coefficient of kinetic friction to govern rather than the coefficient of static friction.

Figure 11A:
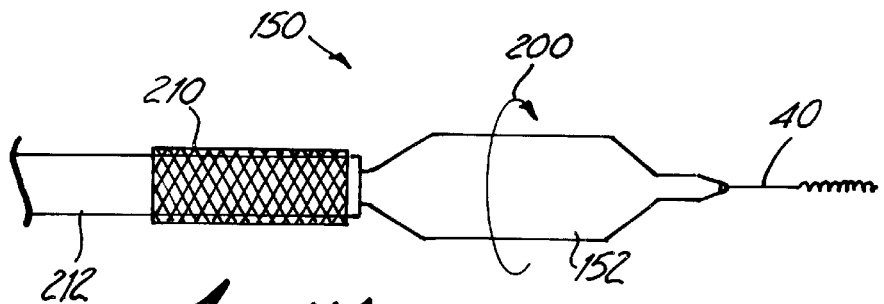
FIG. 11A is a side view of a distal portion of a dilator device in accordance with one embodiment of the present invention.
Figure 11B:
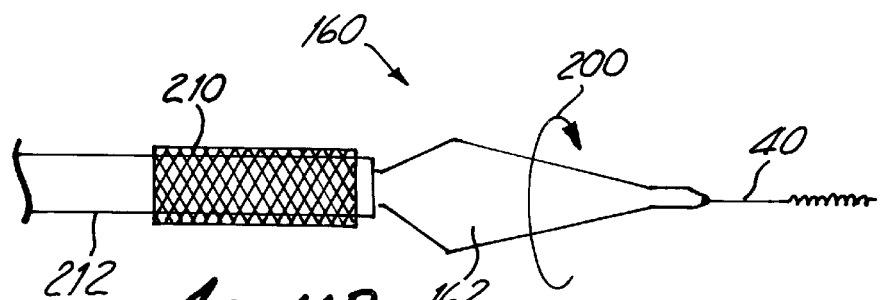
FIG. 11B is a side view of a distal portion of a dilator device in accordance with another embodiment of the present invention.

Dilator devices 150 and 160 as illustrated in FIGS. 11A and 11B respectively each include an inflatable balloon 152, 162 connected to the distal end of an elongate catheter shaft (not visible). The dilator devices 150 and 160 may be modified conventional balloon catheters providing for enhanced torquability such that the device may be rotated. Each of the dilator devices 150 and 160 may be guided over a conventional guidewire 40.

In use, the dilator devices 150 and 160 are advanced to the extravascular opening, preferably over a guidewire 40. Once the balloon 152, 162 is immediately proximate the extravascular opening, the device 150, 160 may be rotated to facilitate passage into the extravascular opening. Preferably, the balloon 152, 162 is in a deflated state upon insertion into the opening. Once the balloon is within the opening, the balloon 152, 162 is inflated by known means. Inflation of the balloon 152, 162 causes the extravascular opening to dilate to the inflated diameter of the balloon 152, 162. Balloon 152 dilates the extravascular opening to a known constant diameter, whereas balloon 162 may dilate the extravascular opening to one of several known diameters due to its tapered profile. Preferably, balloon 152 has a nominal outside diameter and balloon 162 has a proximal outside diameter corresponding to the desired diameter of the extravascular opening and pathway.

Figure 11C:
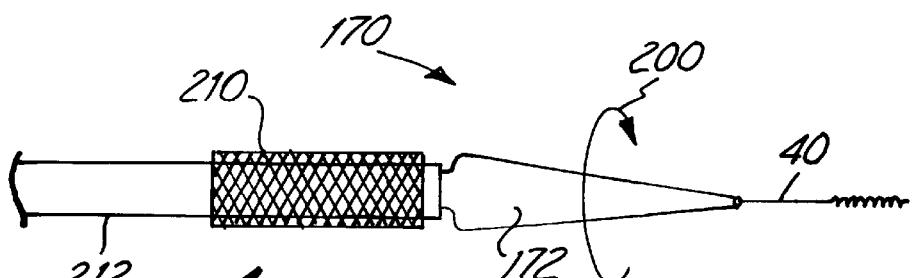
FIG. 11C is a side view of a distal portion of a dilator device in accordance with another embodiment of the present invention.

Dilator device 170 illustrated in FIG. 11C includes a dilator tip 172 that is preferably rigid in the radial direction but flexible along its length. Dilator tip 172 has a distal outside diameter slightly smaller than the initial inside diameter of the extravascular opening and a proximal diameter corresponding to the desired final diameter of the extravascular opening and pathway. With this structure, as the dilator 172 is inserted into the extravascular opening and passageway, the enlarged portion of the dilator 172 causes the opening in passageway to assume a similar diameter. Rotation of the dilator 172 as it passes through the opening and passageway greatly reduce the amount of friction between the dilator 172 and the adjacent tissues.

Figure 11D:
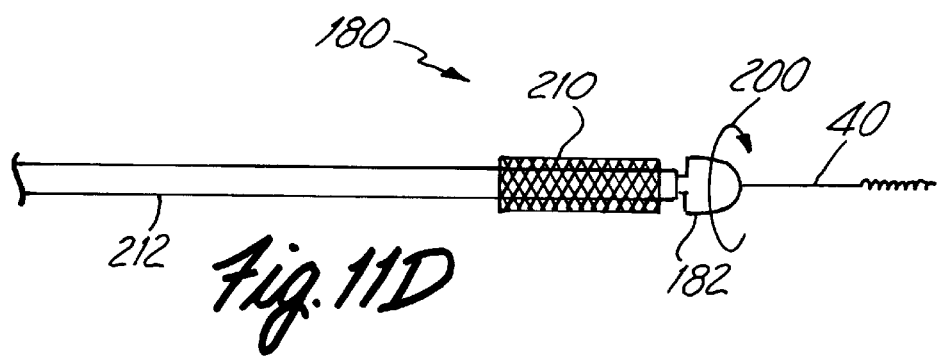
FIG. 11D is a side view of a distal portion of a dilator device in accordance with another embodiment of the present invention.

Dilator device 180 illustrated in FIG. 11D includes a rounded tip 182 that is preferably smooth but may incorporate abrasive material thereon. Rounded tip 182 preferably has a proximal diameter corresponding to the desired final diameter of the extravascular opening and pathway in order to accommodate delivery of the conduit 28 such as stent or graft 210.

In use, dilator devices 170 and 180 are advanced over a guidewire to a position immediately proximate the extravascular opening to be dilated. As the tip 172, 182 is advanced into the opening, the tip 172, 182 is rotated to substantially reduce the amount of resistive friction between the tip 172, 182 and the surrounding tissue. Once the extravascular opening and pathway have been dilated, the dilator 170, 180 may be removed.

Figure 12A:
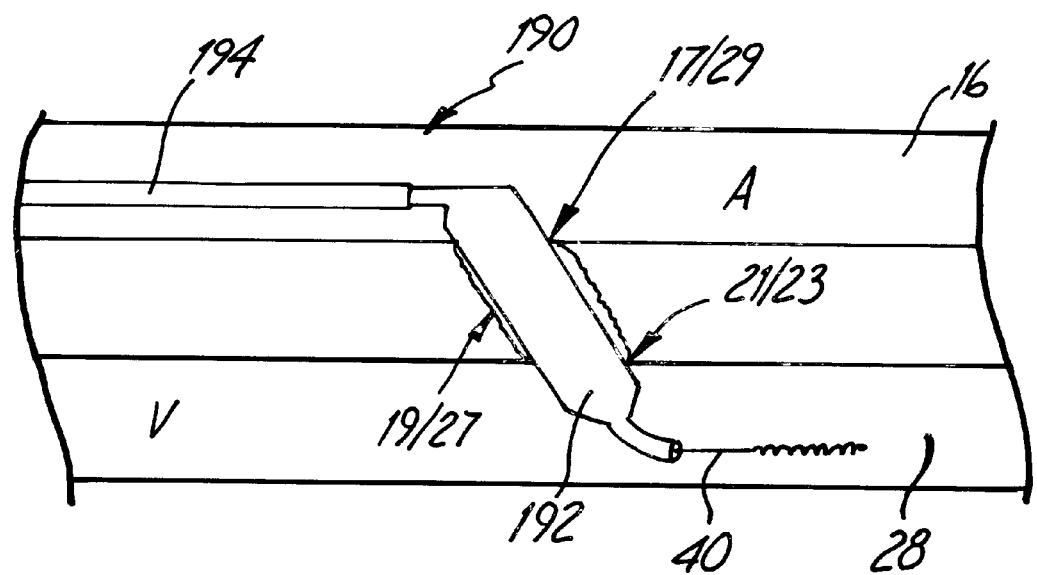
FIGS. 12A and 12B are side views of a distal portion of a dilator and lumen patency device disposed in the coronary vasculature in accordance with one embodiment of the present invention.
Figure 12B:
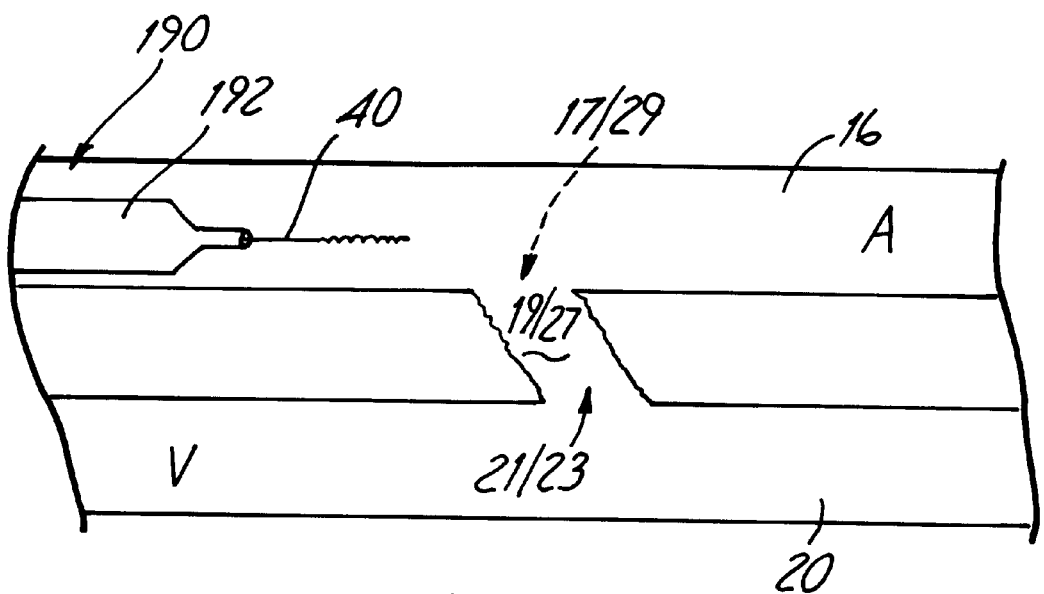

FIGS. 12A and 12B are side views of a distal portion of a dilator and lumen patency device 190 disposed in the coronary vasculature, namely coronary artery 16 and coronary vein 20. Dilator and lumen patency device 190 serves to dilate the extravascular openings and the pathway. The device 190 also serves to maintain the extravascular openings and the pathway by cauterizing the surrounding tissue. The device 190 includes an inflatable balloon 192 connected to the distal end of an elongate shaft 194. The balloon 192 includes means for heating the adjacent tissue such as a metal coating on the exterior of the balloon 192 connected by electrical leads passing through the elongate shaft 194 to an electric power source. The electric power source delivers electrical energy to the metal coating on the balloon 192 in order to generate heat.

The metalized layer on the balloon 192 serves to heat the tissue surrounding the balloon to a sufficient degree to cause cauterization. Other means to cause cauterization may also be utilized. For example, a chemical coating the balloon 192 may be used to chemically cauterize the surrounding tissue. Furthermore, RF energy or light energy (e.g., laser) may be utilized to heat the surrounding tissue. Those skilled in the art will recognize that several means to heat the surrounding tissue may be implemented by known constructions.

In use, the dilator and lumen patency device 190 is preferably advanced over a guidewire 40 into the coronary artery 16 and through the extravascular openings and the pathway. Once the balloon 192 is positioned in the openings and pathway, preferably in the deflated state, the balloon 192 is inflated to enlarge the openings and pathway. Once the openings and pathway are enlarged to a sufficient degree to allow the passage of blood therethrough, the heating means may be activated by applying electrical energy, light energy or the like to the exterior of the balloon 192 thus heating the surrounding tissue. Once the surrounding tissue is heated to a sufficient degree to cause cauterization, the device 190 may be retracted as illustrated in FIG. 12B. After cauterization, the extravascular openings and the pathway remain patent. However, it may be desirable to ensure the patency of the openings and the pathway by utilizing a suitable conduit 28 such as a stent or graft (not shown).

Monitoring Devices

FIGS. 13A–13B, 14A–14B, 15A, 15C–15E, 16, 18A–18B, 19A–19M, 20A–20B, 21A–21B, 22A–22B, 23A–23B, 24A–24B illustrate side views of a distal portion of several tissue penetration monitoring devices 230, 240, 250, 260, 410, 430, 440, 450, 460, 470 disposed in the coronary vasculature. Each of the devices may be independent devices as illustrated or may be incorporated into one or more of the devices discussed previously. For example, each of the devices 230, 240, 250, 260, 440 may be incorporated into the tissue penetrating member 46, 310 as used with device 30, 70, 90, 100, 110, 120, 130, 140 and 300. For purposes of illustration only, and for sake of simplicity, the devices 230, 240, 250 and 260 are illustrated tissue penetrating members.

Figure 13A:
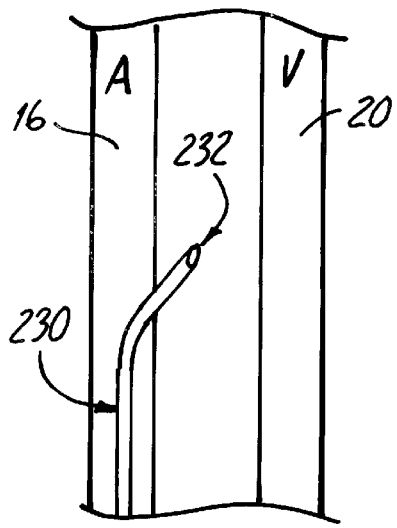
FIGS. 13A and 13B are side views of a distal portion of a tissue penetration monitoring device disposed in the coronary vasculature in accordance with one embodiment of the present invention.
Figure 13B:
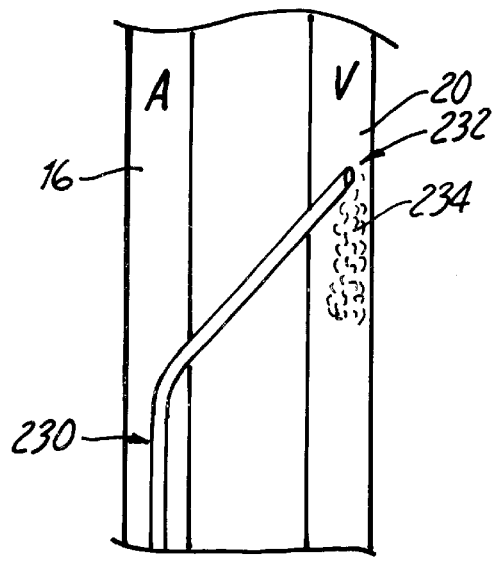

FIGS. 13A and 13B illustrate a side view of a distal portion of a tissue penetration monitoring device 230 disposed in the coronary vasculature 16, 20. The device 230 includes a lumen extending therethrough such that a source of contrast media may be injected from the proximal end of the device outside the patient's body to the distal opening 232. In use, as the device 230 passes from the coronary artery 16 to the coronary vein 20 (or vice versa) the source of pressurized contrast media is applied to the proximal end of the device 230. Accordingly, when the distal opening 232 passes into the lumen of the coronary vein 20, the pressurized contrast media 234 flows into the venous lumen. The radiopaque contrast media 234 is visible under fluoroscopy such that the treating physician knows when the extravascular openings and the pathway have been defined connecting the coronary artery 16 and the coronary vein 20 when a cloud of contrast dye 234 is visible on the x-ray fluoroscopy display. In this manner, the treating physician may monitor the progress of creating the extravascular openings and the pathway and stop the tissue penetrating member as appropriate. After the extravascular openings and pathway are created, the device 230 may be removed.

Figure 14A:
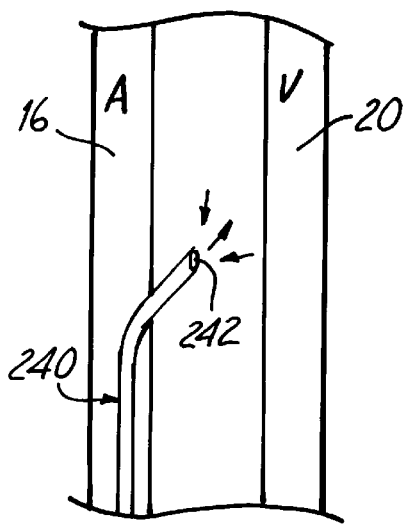
FIGS. 14A and 14B are side views of a distal portion of a tissue penetration monitoring device disposed in the coronary vasculature in accordance with another embodiment of the present invention.
Figure 14B:
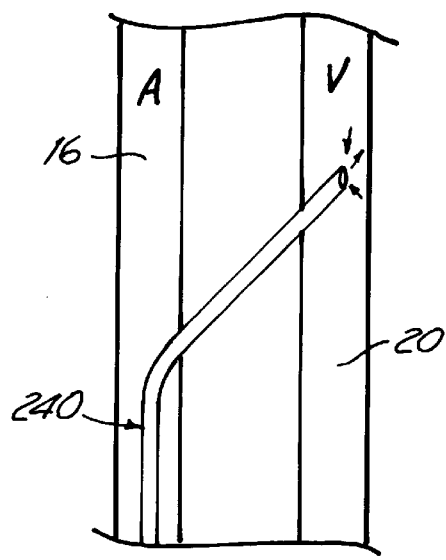

FIGS. 14A and 14B are side views of a distal portion of a tissue penetration monitoring device 240 disposed in the coronary vasculature 16, 20. Monitoring device 240 is substantially similar to device 230 except as described herein. Device 240 includes a light guide disposed throughout its entire length, extending from a light source (e.g. laser) outside the patient to the distal opening 242. The light source may be any infrared wavelength of light for tissue penetration. For example, the light source may be a light emitting diode (LED) or laser source.

As the device 240 is advanced out the coronary artery towards the coronary vein 20, light is transmitted through one element of the light guide and out the distal opening 242. The light reflected from tissue adjacent the opening 242 is received by the light guide. In this manner, the light signal transmitted through the light guide exits the distal tip 242, is reflected off of adjacent tissue, is transmitted back through the light guide and is received by an optical sensor. The light source and the optical sensor are not illustrated for purposes of simplicity, but will be readily understood by those skilled in the art.

The reflected light signal is then measured as to its intensity and/or frequency and may be compared to the transmitted light signal. Because different body tissues have different reflective properties, the intensity and/or frequency of the reflected light signal is indicative of the tissue adjacent the opening 242. As such, as the device 240 passes through the tissue surrounding the coronary vasculature, a signal is received indicating the type of tissue being penetrated. When the distal end of the device 240 enters the lumen of the coronary vein 20, the reflected light signal indicates the presence of blood (as opposed to tissue), thus indicating that a pathway has been established between the coronary artery 16 and the coronary vein 20.

Figure 14C:
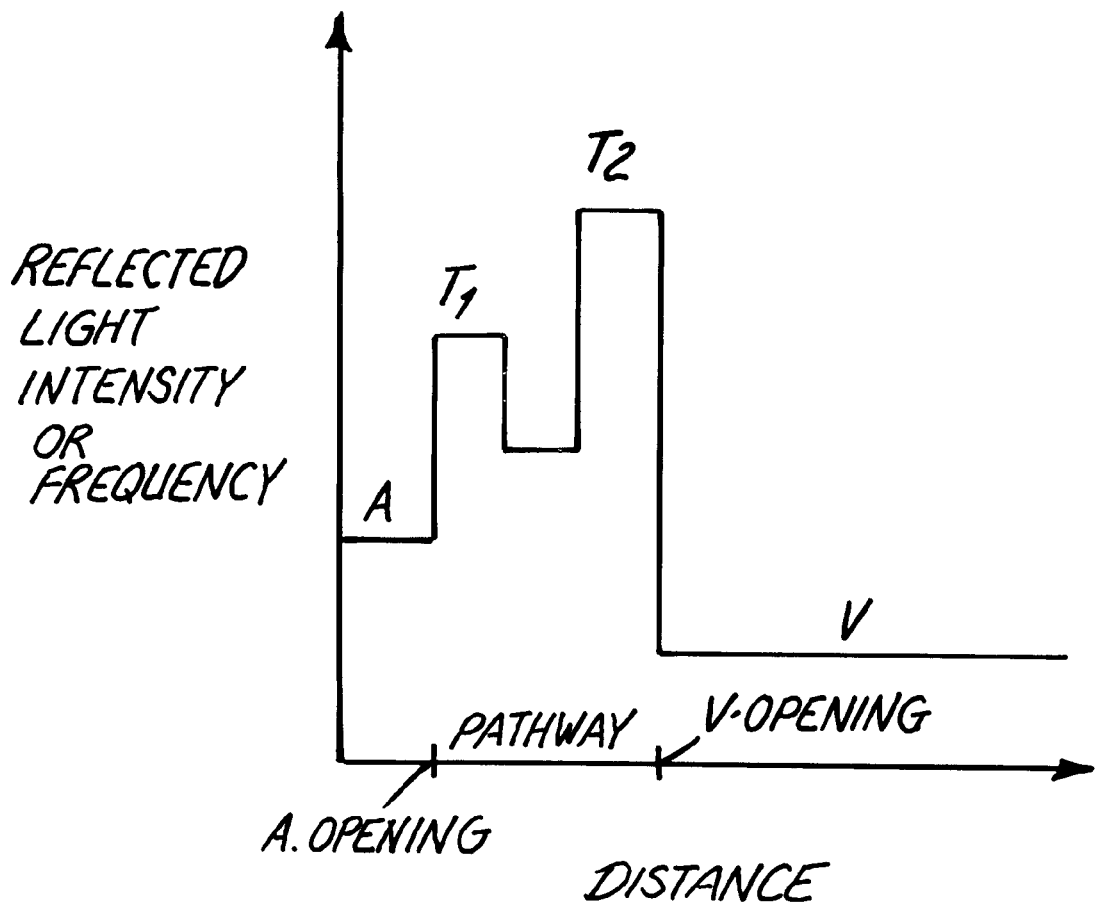
FIG. 14C is a graph illustrating a parameter as a function of distance as measured by the device illustrated in FIGS. 14A and 14B.

FIG. 14C illustrates the measured reflected light signal as a function of distance. The distance indicated on the horizontal axis represents the distance the distal end of the device 240 has been advanced. As mentioned previously, the reflected light intensity and/or frequency may be measured. Initially, the reflected light signal indicates the presence of arterial blood as indicated by the letter "A". As the distal end of the device 240 passes through tissue, the measured reflected light signal has a different value as indicated by the letters "T1" and "T2". When the distal end of the device 240 enters the lumen of the coronary vein 20, yet another reflected light signal is measured as indicated by the value "V". Accordingly, the treating physician may monitor the progress of creating the extravascular openings and pathway as indicated by the measured reflected light signal.

Figure 15A:
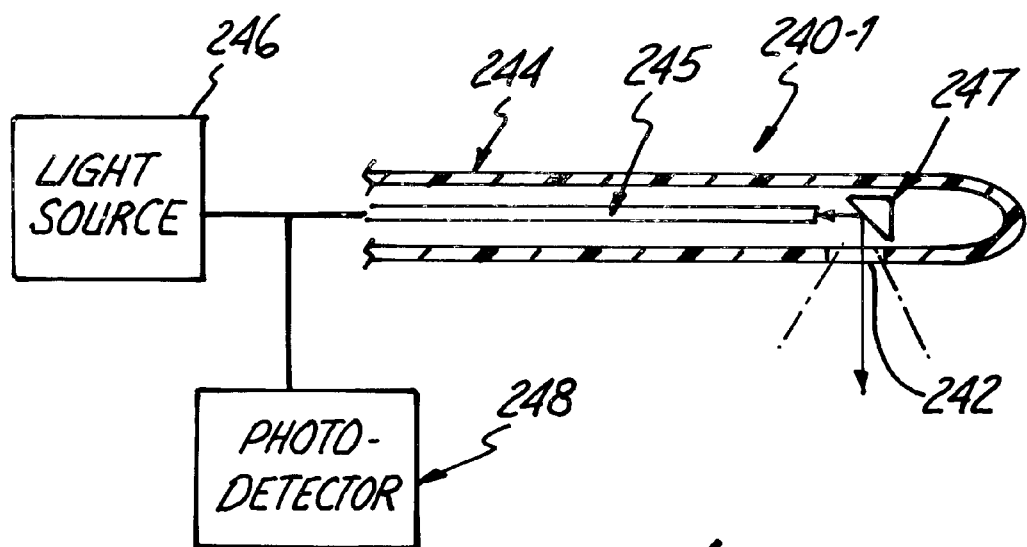
FIG. 15A illustrates an embodiment of a tissue penetrating monitoring device.
Figure 15B:
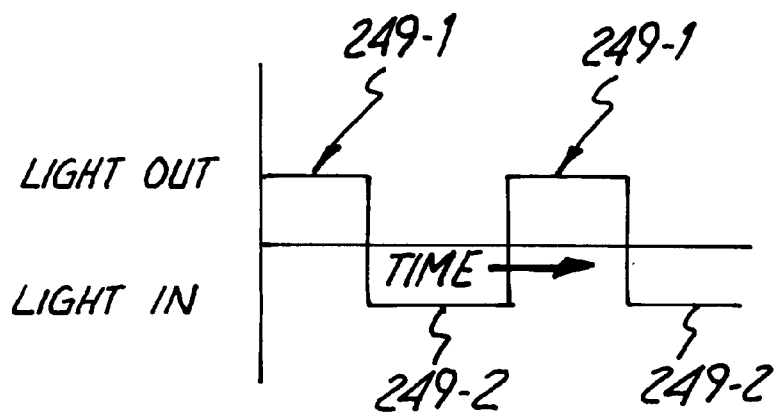
FIG. 15B graphically illustrates synchronization of transmitting and receiving functions of a monitoring device of the type illustrated in FIG. 15A.

The light guide may be a singular element capable of transmitting and receiving light signals, or may be multiple elements for transmitting and receiving light signals separately. Preferably, two or more elements are utilized in the light guide to separately transmit and receive light signals. FIGS. 15A–15E illustrate various embodiments of monitoring devices 240 incorporating a transmitter and a receiver where like numbers are used to identify like parts. Device 240-1 includes an elongated shaft 244 including a distal opening 242. A fiber optical cable 245 extends along the length of the shaft 244 to transmit and receive light from a light source 246. Distal opening 242 is transversely located and device 240-1 includes mirror 247 to direct light transmitted via cable 245 out opening 242 or to receive light to cable 245 through transverse opening 242. Light received is transmitted along cable 245 to a photo detector or sensor 248. Light is alternately transmitted 249-1 and received 249-2 as illustrated in FIG. 15B. Preferably, transmission and reception is controlled by a processor coupled to the light source 246 and detector 248.

Figure 15C:
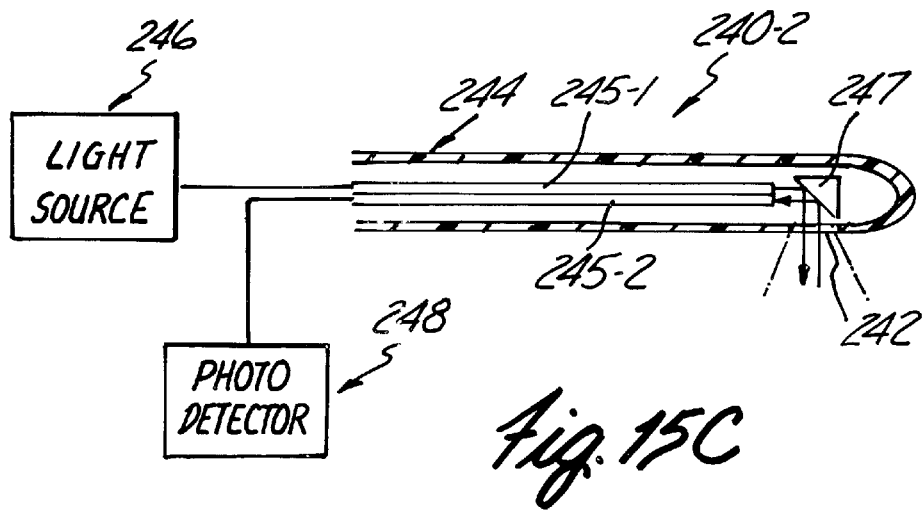
FIGS. 15C–15E illustrate alternate embodiments of a tissue penetrating monitoring device.
Figure 15D:
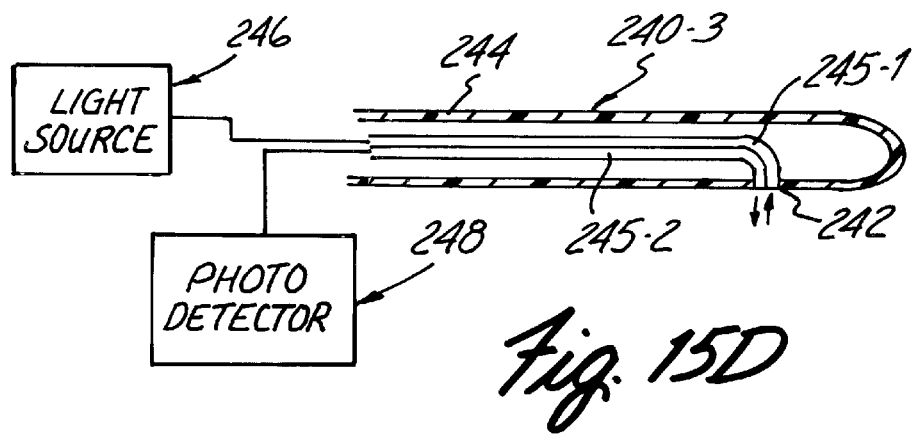

FIG. 15C illustrates another device 240-2 including multiple fiber cables 245-1, 245-2 for transmitting light and receiving reflected light. Thus light is transmitted along cable 245-1 and transmitted out opening 242 via mirror 247 and is received through opening and transmitted along cable 245-2 via mirror 247 for analysis. FIG. 15D illustrates another monitoring device 240-3 embodiment. Device 240-3 in FIG. 15D includes multiple cables 245-1, 245-2 where cables 2451, 245-2 are bent to align ends of cables 245-1, 245-2 with traverse opening 242 for transmitting and receiving light.

Figure 15E:
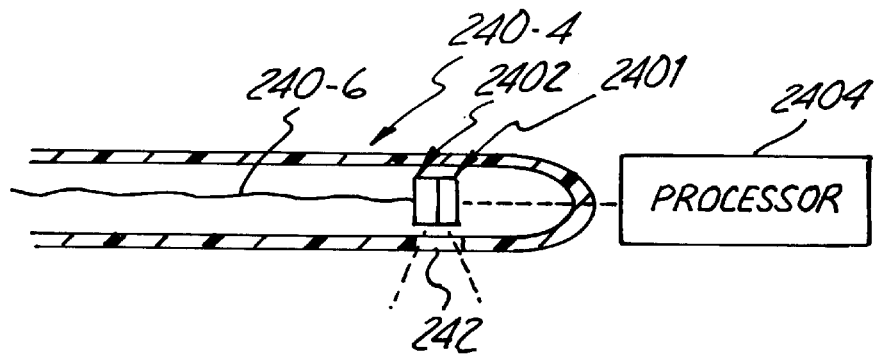

FIG. 15E illustrates an alternate embodiment 240-4. As shown, light source is an LED 2401. Light is transmitted from LED 2401 and detected by a photodiode 2402. Detection and transmission of light is synchronously controlled via processor 2402. A wire 2406 electrically connects processor 2404, LED 2401 and photodiode 2402 to an external power source and monitor for operation.

Operation of LED 2401 and photo detector 2402 can be synchronized as illustrated in FIG. 15B where light is sequentially transmitted 249-1 and received 249-2. Although FIGS. 15A–15D illustrate multiple embodiments of device 240 for transmitting and receiving light for monitoring operations, it should be understood that these embodiments are examples and alternate embodiments may be used. In the embodiments shown, the monitoring device can be incorporated with the tissue penetrating member at a distal end of the device 240 in combination with transverse opening 242 or member can be slideably disposed in shaft 244 and exit opening 242 for penetrating operation. Although FIGS. 15C–15E illustrate a single device for transmitting and receiving light, separate devices can be inserted or used and device 240 can be a separate device or incorporated with the tissue penetrating device or other treatment devices.

Figure 16:
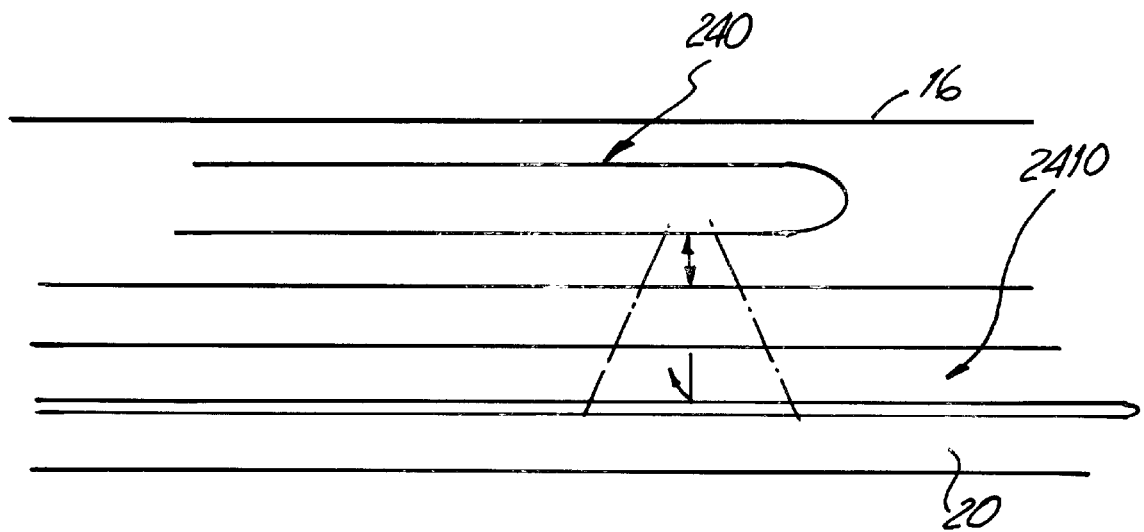
FIG. 16 illustrates an alternate embodiment for monitoring operation of a tissue penetrating device.

FIG. 16 illustrates another embodiment for monitoring position. As shown in FIG. 16, a reflective catheter 2410 is inserted into vein 20. Light is transmitted from device 240. When penetrating device has accessed vein 20, light reflected from catheter 2410 having known reflective properties is used to verify access to vein 20 at a penetrating site. Example reflective materials may be gold or silver.

Figure 17:
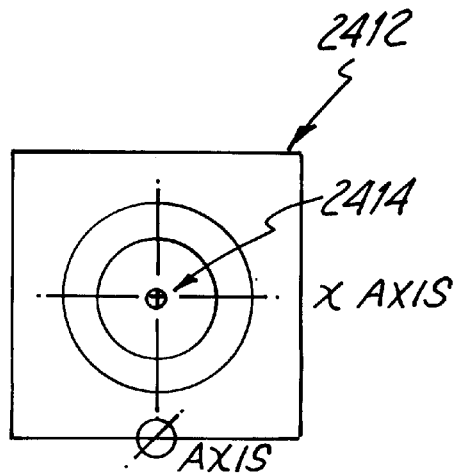
FIG. 17 illustrates a monitor for observing progress of the tissue penetrating device.

As shown in FIG. 17, progress of the penetrating member may be observed via a monitor 2412 which can be programmed to display penetrating member position relative to target 2414 (e.g. vein 20) based upon data received from the monitoring device to gauge the relative distance of the penetrating device from the vein 20. Monitor 2412 visually displays position of device 240 relative to the target 2414 based upon the signal measured by the monitoring device and actual signal at target 2414.

Figure 18A:
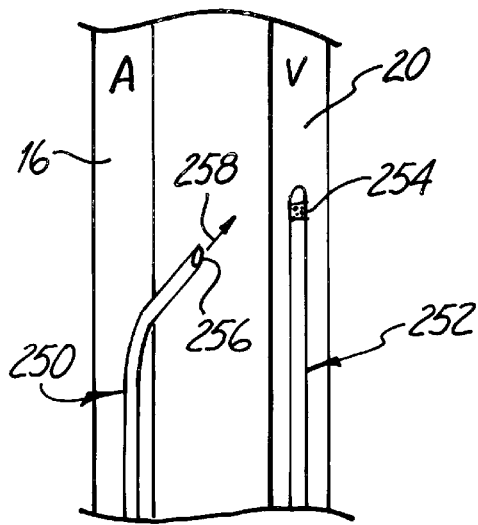
FIGS. 18A and 18B are side views of a distal portion of a tissue penetration monitoring device disposed in the coronary vasculature in accordance with another embodiment of the present invention.
Figure 18B:
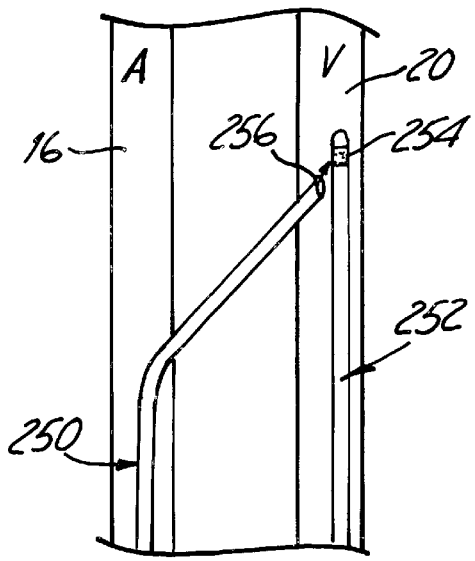

FIGS. 18A and 18B illustrate side views of a distal portion of a tissue penetration monitoring device 250 disposed in the coronary vasculature 16, 20. Device 250 is used in conjunction with a light sensing device 252 including a light sensor 254 disposed on the distal end thereof. The principals of operation of device 250 and device 252 are similar to device 240 except as described herein.

Device 250 includes an optical guide such as a fiber optic guide extending along the entire length of the device. Proximal end of the light guide (not visible) is connected to a light source (e.g. laser) such that light may be transmitted from the light source, through the light guide and out the distal end 256 of the device 250. The light exiting the distal end 256 of the device 250 is indicated by arrow 258. This light signal 258 is received by light transducer 254 which transmits,an electrical signal through electrical leads in the elongate shaft of device 252 to a means for measuring the electrical signal disposed outside the patient's body. The electrical signal produced by transducer 254 is indicative of the intensity of the light signal 258 exiting the distal end 256 of the device 250. Accordingly, as the device 250 comes closer to the light transducer 254 disposed in the coronary vein 20, the electrical signal generated by the transducer 254 increases. Thus, as illustrated in FIGS. 18A–18B, transmitter and receiver are incorporated in separate devices and inserted into the bypassed conduit and bypass conduit for operation.

Figure 18C:
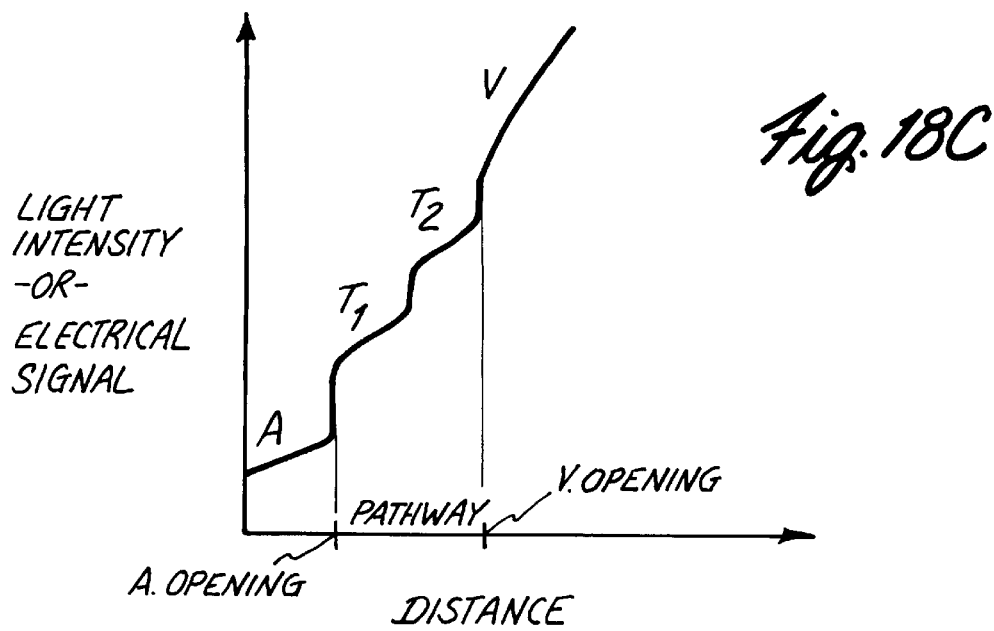
FIG. 18C is a graph illustrating a parameter as a function of distance as measured by the device illustrated in FIGS. 18A and 18B.

An example of the signal as measured by device 252 is illustrated in FIG. 18C. Because the light intensity measured by the transducer 254 is proportional to the electrical signal generated by the transducer 254, the graph shown in FIG. 18C illustrates both the light intensity and electrical signal as a function of distance. The distance indicated on the horizontal axis represents the distance the distal end of the device has been advanced. When the distal end 256 of the device 250 is in the coronary artery 216, a relatively low signal is received by the transducer 254 as indicated by the letter "A". As the distal end 256 of the device 250 passes through the vascular tissue and the surrounding heart tissue, the relative light intensity or electrical signal of transducer 254 increases as indicated by the letters "T1" and "T2". When the distal end 256 of the device 250 is in the lumen of the coronary vein 20 as illustrated in FIG. 18B, the light intensity or electrical signal on the transducer 254 reaches a maximum as indicated the letter "V". With this arrangement, the treating physician may monitor the progress of the device 250 as it creates the extravascular openings and pathway. When the extravascular openings and pathway have been successfully created, the treating physician may stop the penetration and remove the device 250.

Figure 19A:
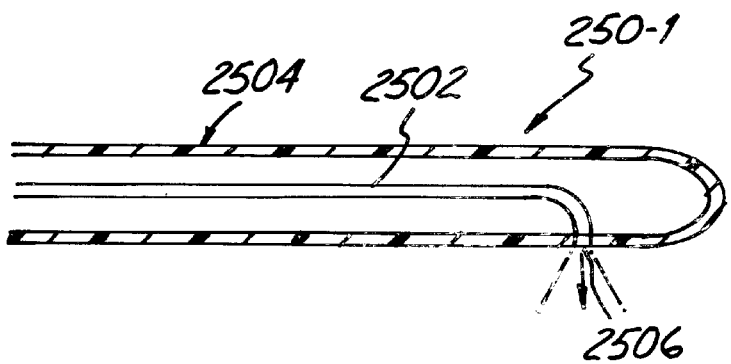
FIGS. 19A–19M illustrate various embodiments of transmitting devices for a monitoring system illustrated in FIGS. 18A–18B.
Figure 19B:
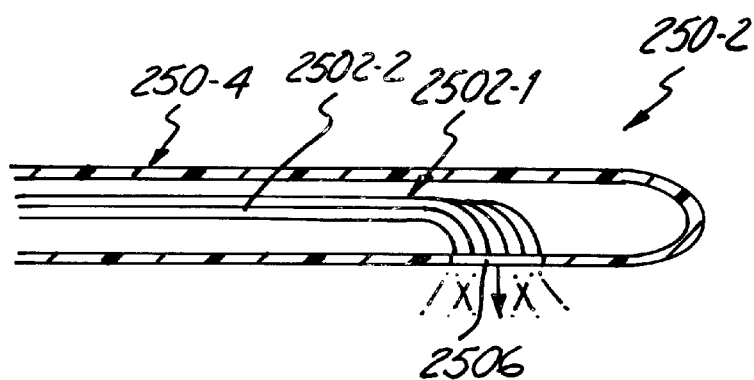
Figure 19C:
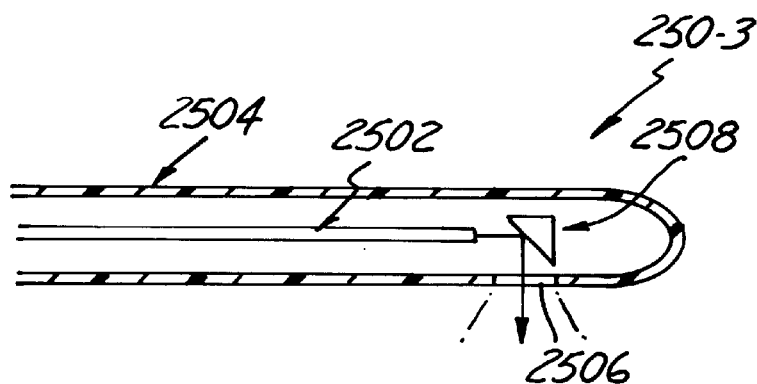
Figure 19D:
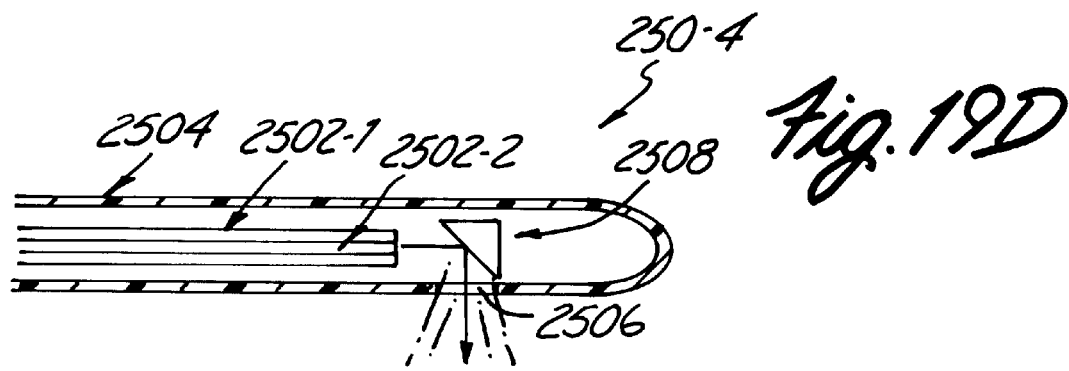

FIGS. 19A–19M illustrate alternate embodiments of device 250 insertable into the bypassed conduit (e.g. artery 16). As shown in FIG. 19A, device 250-1 including fiber optical cable 2502 extending along shaft 2504 to transmit light from a light source (not shown) through transverse opening 2506 to receiver or device 252 disposed in vein 20. As shown, end of cable 2502 is bent to align with opening 2506. FIG. 19B illustrates a device 250-2 including multiple cables 2502-1, 2502-2. FIG. 19C illustrates a device 250-3 including mirror 2508 to direct light from cable 2502 through transverse opening 2506. FIG. 19D illustrates a similar device 250-4 having multiple cables 2502-1, 2502-2 and mirror 2508 for directing light through opening 2506.

Figure 19E:
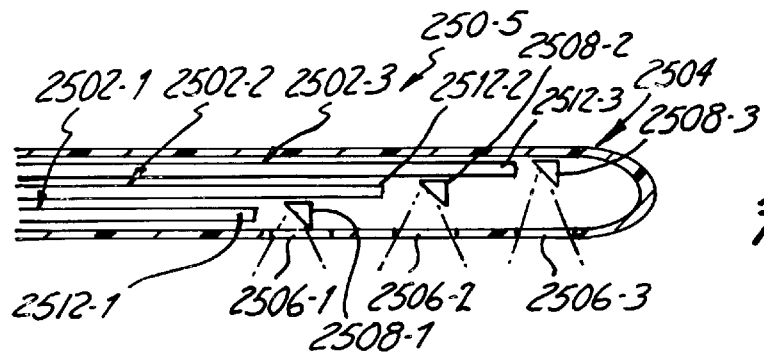

FIG. 19E illustrates an alternative embodiment 250-5 including multiple cables 2502-1, 2502-2, 2502-3 having a plurality of staggered ends 2512-1, 2512-2, 2512-3 and mirrors 2508-1, 2508-2, 2508-3 for transmitting light through multiple openings 2506-1, 2506-2, 2506-3 staggered along the length of shaft 2504. Light transmitted through cables 2502-1, 2502-2, 2502-3 may be the same or differing wavelengths. For the same wavelength, position is monitored by the intensity of the light and for differing wavelengths, the frequency and intensity is measured to determine position based upon the known frequencies of the various cables 2502-1, 2502-2, 2502-3.

Figure 19F:
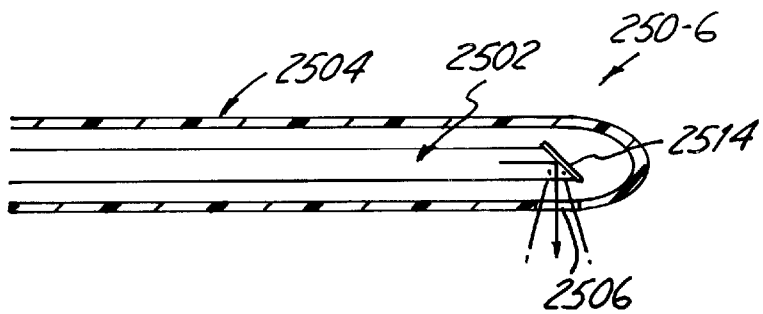
Figure 19G:
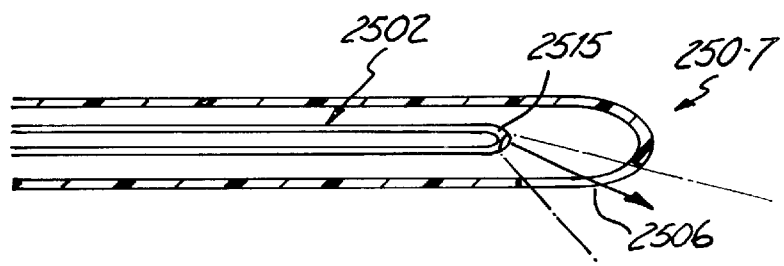
Figure 19H:
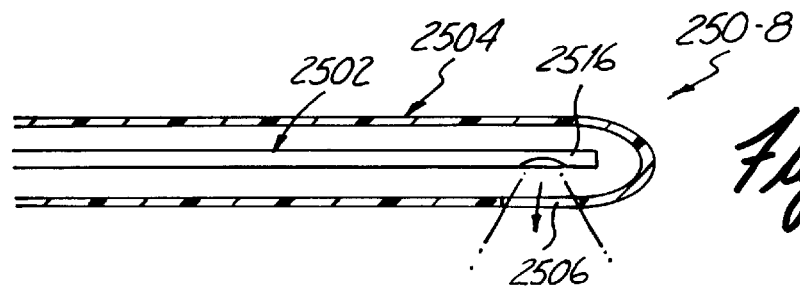
Figure 19I:
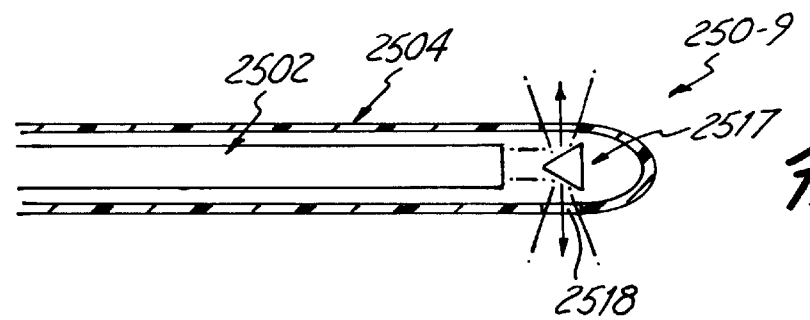
Figure 19J:
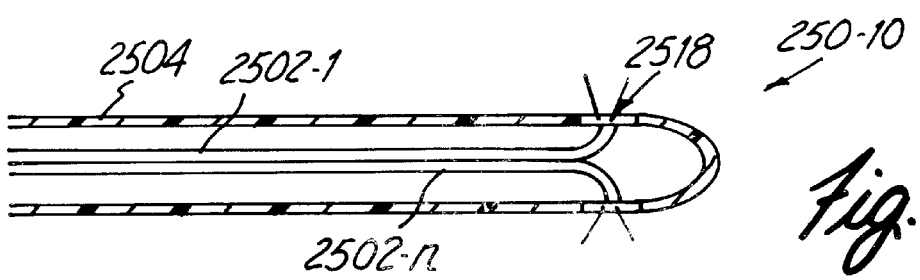

As shown in FIG. 19F in an alternate embodiment 250-6, an end of cable 2502 may have a coated reflected end 2514 to dispense light through a transverse opening 2506, or as shown, in FIG. 19G in embodiment 250-7, the fiber cable may be tightly bent at 2515 so that the light leaks to transmit light. In embodiment 250-8 in FIG. 19T, fiber cladding may be removed to transmit light from the cable 2502. Alternatively, in embodiment 250-9 in FIG. 19I, a cone shaped mirror 2517 may be aligned with cable end 2502 to circumferentially disperse light through a circumferential opening 2518 or as shown in embodiment 250-10 in FIG. 19J multiple cables 2502-1, 2502-2 can be bent so that ends circumferentially disperse light through opening 2519 which can be circumferential or can include multiple dispersed openings about the perimeter of shaft 2504.

Figure 19K:
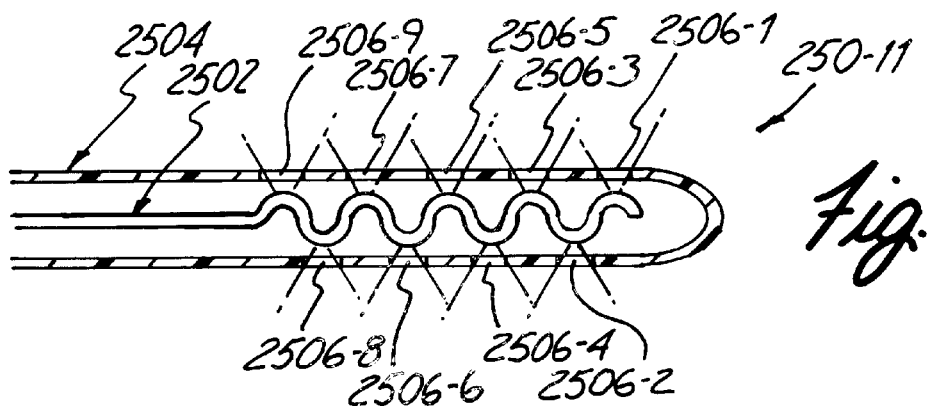
Figure 19L:
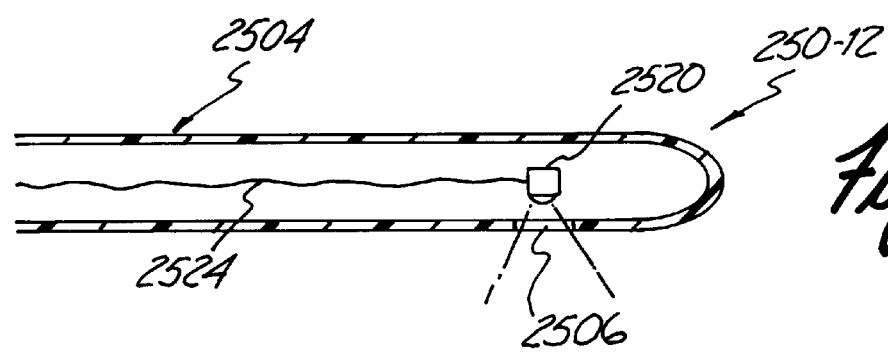
Figure 19M:
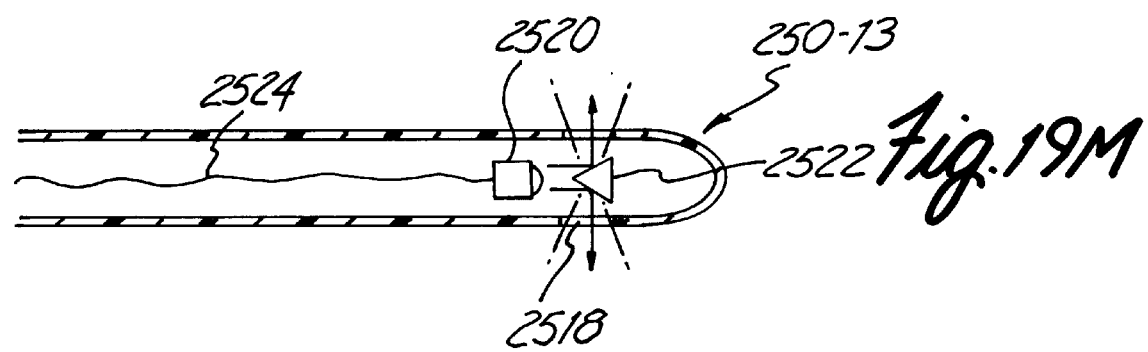

As shown in FIG. 19K, in device 250-11, cable 2502 is sinusoidally bent along a length thereof to define a plurality of light dispersing positions for transmitting light through a plurality of spaced openings 2506-1, 2506-2, 2506-n through shaft 2504. Alternatively, embodiment 250-12 shown in FIG. 19L includes an LED 2520 light source to disperse light through opening 2506 or embodiment 250-13 includes an LED 2520 which projects light to a cone shaped mirror 2522 to circumferentially disperse light through circumferential opening 2518. A wire 2524 electrically connects LED 2520 to a power source. In the embodiments shown, device 250 can be incorporated with the penetrating device having a penetrating member at a distal end of shaft 2502 and light transmitting opening 2506 transverse and spaced from the distal end or alternatively penetrating member may extend through a lumen through shaft 2502 and exit distal opening 2506, 2518, 2519.

Figure 20A:
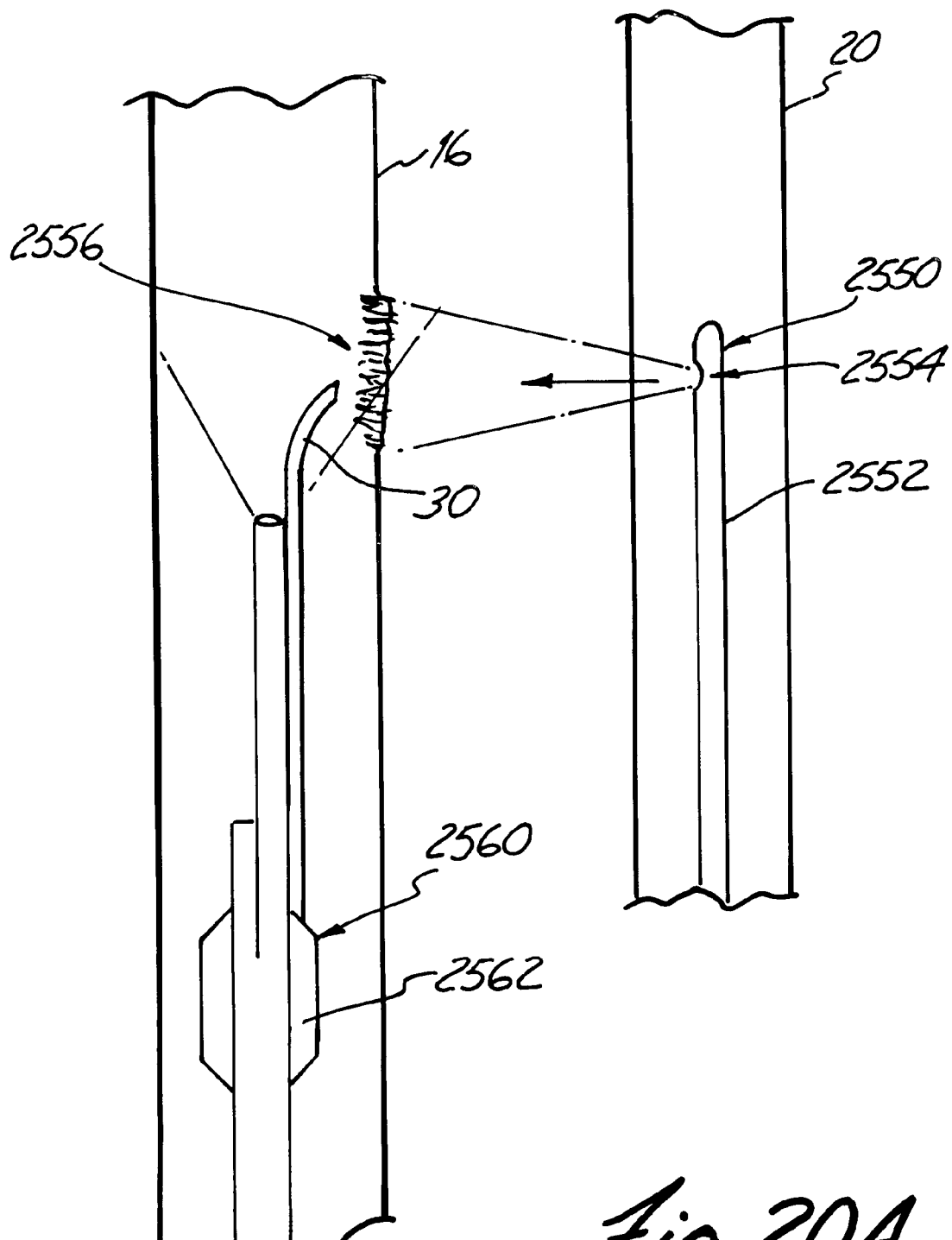
FIGS. 20A–20B illustrate an alternate embodiment of a tissue penetration monitoring assembly.
Figure 20B:
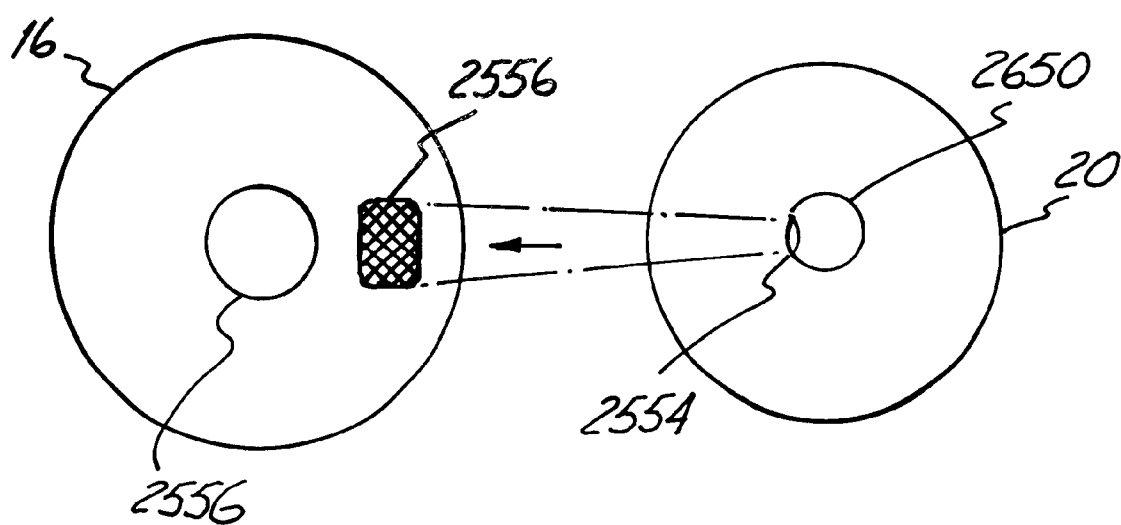

FIGS. 20A–20B illustrate a locating device for locating a penetrating device or member. As shown, the locating device includes a light source transmitter 2550 which includes an elongated shaft 2552 insertable into a vein 20 to a bypass site. As shown, shaft 2552 includes a distal opening 2554 through which light is transmitted to illuminate or otherwise locate a piercing or bypass site 2556 as illustrated in FIGS. 20A–20B. An optical detection or angioscope (not separately shown) detects site 2556 illuminated by the light source transmitter 2550. In the embodiment shown, the angioscope is incorporated with the penetrating device or member in a single catheter device 2560 for insertion. Detection of site 2556 is accomplished by measuring the intensity of the light detected by the angioscope to locate penetrating device or member to puncture vessel 16 for the bypass operation. In the embodiment shown, device 2560 includes an occlusion balloon 2562 for piercing operation.

Figure 21A:
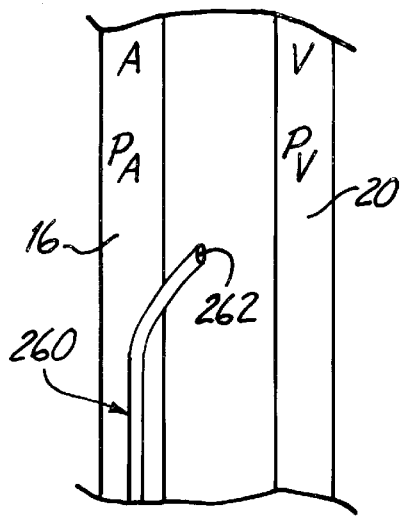
FIGS. 21A and 21B are side views of a distal portion of a tissue penetration monitoring device disposed in the coronary vasculature in accordance with yet another embodiment of the present invention.
Figure 21B:
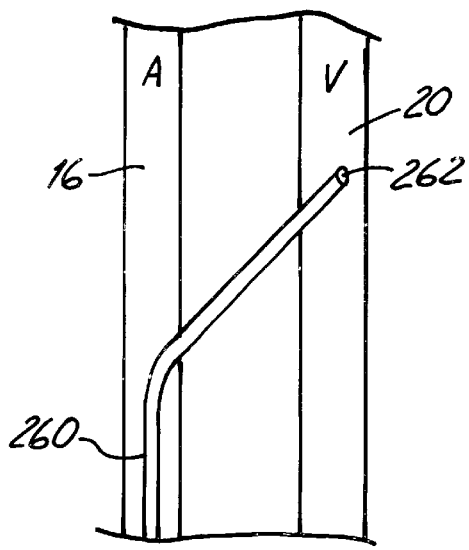

FIGS. 21A and 21B are side views of a distal portion of a tissue penetration monitoring device 260 disposed in the coronary vasculature 16, 20. The device 260 includes a lumen extending the entire length of the device such that the pressure at the distal opening 262 may be measured at the proximal end (not shown) of the device 260. Except as described herein, the device 260 is substantially similar to device 230 illustrated in FIGS. 13A and 13B.

The pressure inside the coronary artery 16 is represented by $P_a$ and the pressure inside the coronary vein 20 is represented by $P_v$. Typically, $P_a$ is greater than $P_v$. The vascular pressure $P_a$, $P_v$ may be measured at the distal end 262 of the device 260 utilizing suitable pressure monitoring devices located at the proximal end (not shown) of the device 260. Such pressure monitoring devices include, but are not limited to, pressure transducers and pressure gauges having sufficient sensitivity to measure and monitor vascular pressure gradients on the order of 0.1 psi.

Figure 21C:
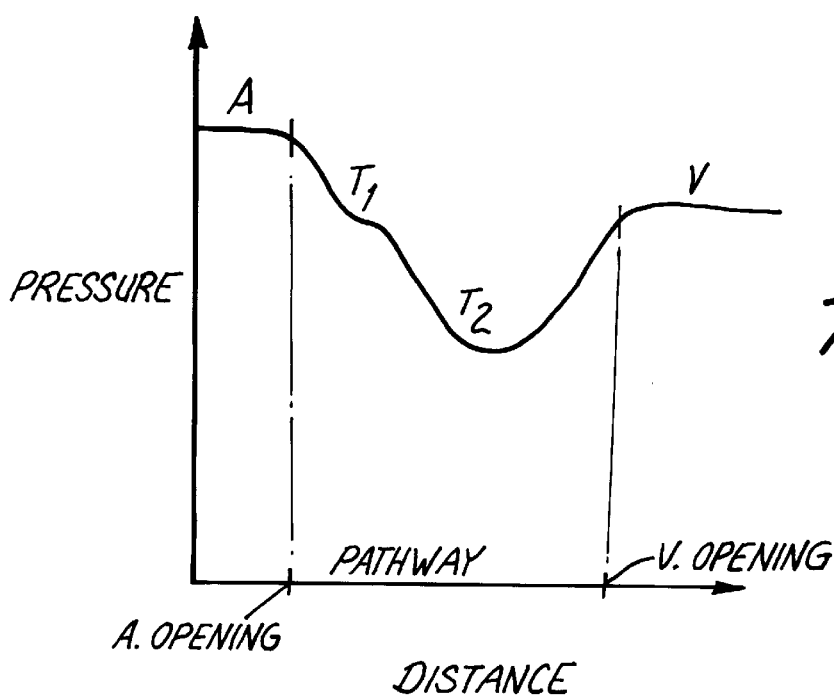
FIG. 21C is a graph illustrating a parameter as a function of distance as measured by the device illustrated in FIGS. 21A and 21B.

With reference to FIG. 21C, as the device 260 is advanced from the coronary artery 16 to the coronary vein 20, as indicated on the horizontal axis, the pressure at the distal end 262 of the device 260 is monitored. Initially, with the distal end 262 in the coronary artery 16, the pressure is at its maximum as indicated by the letter "A". As the device 260 passes through the vascular tissue and the muscular tissue of the heart, the relative pressure decreases as indicated by the letters "T1" and "T2". When the distal end 262 is in the lumen of the coronary vein 20 as illustrated in FIG. 21B, the relative pressure increases to the level indicated by the letter "V". In this manner, the treating physician may monitor the progress of the distal end 262 as it passes from the coronary artery 16 to the coronary vein 20. When the extravascular openings and the pathway have been established as desired, the treating physician may stop the penetration procedure and withdraw the device 260.

FIGS. 22A, 22B, 23A, 23B, 24A and 24B illustrate various tissue penetration alignment and monitoring devices disposed in the coronary vasculature that utilize intravascular ultrasound (IVUS) technology. IVUS technology is well known in the art and the specifics of such technology have been omitted for sake of clarity. As described herein, the IVUS technology may be used to establish the proper alignment for the tissue penetrating member, establish the distance and position of the target site, and/or monitor the progress of the tissue penetrating member as it is advanced to the target site. Accordingly, various features of each of the devices disclosing FIGS. 22A, 22B, 23A, 23B, 24A and 24B may be combined or separated to provide one or more of these functions as desired.

Figure 22A:
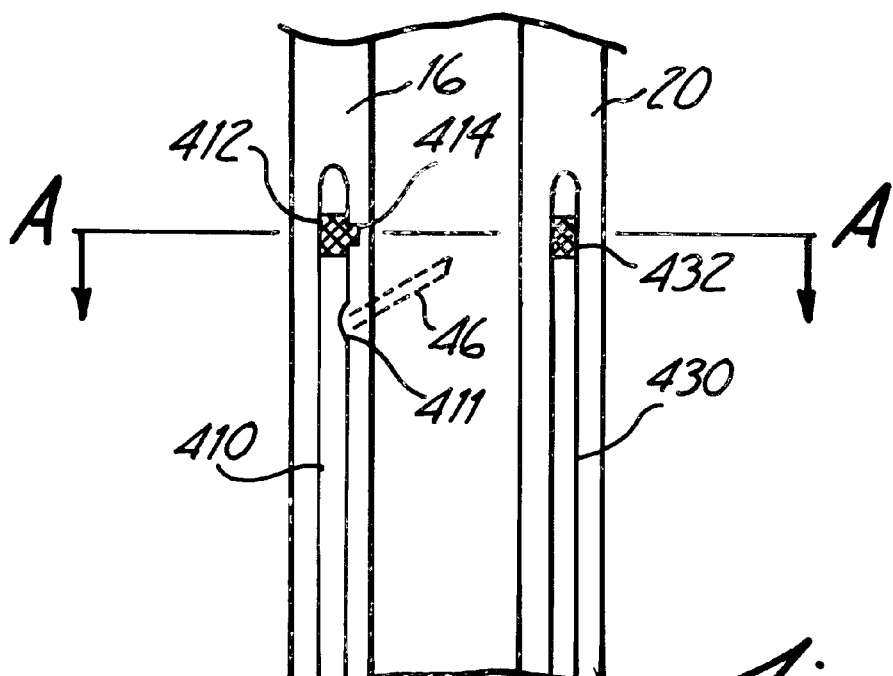
FIG. 22A is a side view of a distal portion of tissue penetration alignment and monitoring devices disposed in the coronary vasculature in accordance with one embodiment of the present invention.

FIG. 22A illustrates a side view of a distal portion of tissue penetration alignment and monitoring devices 410 and 430 disposed in the coronary vasculature 16, 20 in accordance with one embodiment of the present invention. Tissue penetration alignment and monitoring device 410 includes an ultrasonic transducer 412 disposed at the distal end thereof. As used herein, the term ultrasonic transducer may include an ultrasonic transmitter, an ultrasonic receiver, or an ultrasonic transmitter and receiver, unless otherwise specified. Device 410 also includes an alignment marker 414 disposed adjacent the ultrasonic transducer 412. The alignment marker 414 may be any suitable echogenic material such as a stainless steel wire or an ultrasonic reflective coating disposed on the outer portion of the catheter 410. Tissue penetration alignment and monitoring catheter 410 also includes a tissue penetration member exit port 411 in alignment with the marker 414. A tissue penetration member 46 exits the port 411 in the same plane as the alignment marker 414. Accordingly, the tissue penetration member 46 exiting port 411 follows a path that is substantially coplanar with the position of the alignment marker 414.

In use, the ultrasonic transducer 412 has a field of view 416 which includes the coronary artery 16 and coronary vein 20 as seen in FIG. 17B. Because the alignment marker 414 is made of an ultrasonic reflective coating or other echogenic material, a shadow 418 is cast indicating the angular alignment of the catheter 410. The shadow 418 is substantially coplanar with the path of the tissue penetrating member 46 exiting the port 411. With this arrangement, it is possible to line-up the port 411 by rotating the catheter 410 while viewing the IVUS image and in particular the shadow 418 to establish the proper path for tissue penetrating member 46. The proper path for the tissue penetrating member 46 is established by aligning the shadow 418 as cast by the marker 414 with the target site, namely the coronary vein 20.

For purposes of alignment, the ultrasonic transducer 412 is preferably a transmitter and receiver. With this arrangement, it is possible to establish the proper alignment with the target site without the need for an additional device in the target lumen, such as device 430. However, the transducer 412 may be a transmitter and the transducer 432 on device 430 may be a receiver, or vice-versa.

It is contemplated that the alignment marker 414 may be incorporated into any of the ultrasonic devices discussed herein, including those embodiments that utilize devices in both the native lumen (e.g., artery 16) and the target lumen (e.g., vein 20). For purposes of illustration only, alignment marker 414 is illustrated on device 410, but may be used on device 440, 450, 460, 470, for example. The purpose of alignment marker 414 is simply to aim the tissue penetration member.

Figure 22B:
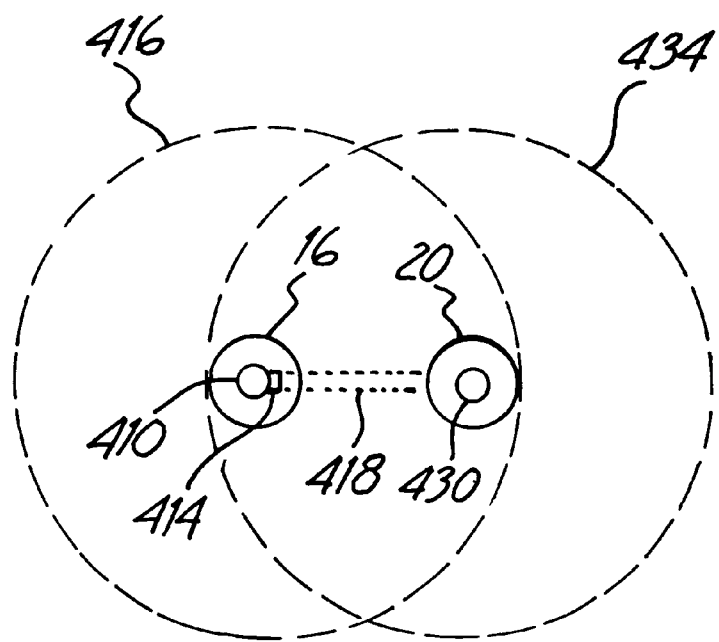
FIG. 22B represents a field of view of the devices illustrated in FIG. 22A along plane A—A.

For purposes of monitoring the formation of the extravascular openings and pathway, the devices 410 and 430 illustrated in FIGS. 22A and 22B may be active or passive ultrasonic devices. As used herein, active ultrasonic devices include devices that have an ultrasonic transducer for transmitting, receiving, or transmitting and receiving ultrasonic signals. Furthermore, the active ultrasonic devices may be categorized into directional, mechanical 360° rotational and phased array. A directional ultrasonic device has a field of view comprising a fixed angle of less than 360°, and typically less than 90°. By contrast, mechanical 360° rotational and phased array have a field of view comprising a full circle (as opposed to an angular segment of the full circle) and are considered to sense more angularity. Those skilled in the art will recognize that the viewing range on mechanical 360° rotational and phased array ultrasonic devices may be modified to include sizes from approximately 30° to as much as 360°.

Passive ultrasonic devices include devices that reflect an ultrasonic signal to indicate its position and/or size. Examples of passive ultrasonic devices include catheters and wires incorporating a passive element comprising an echogenic material. Examples of echogenic materials include ultrasonic reflective coatings (e.g., microbubbles), knurled materials, fileted materials, roughened surface materials, patterned surfaces (e.g., three-dimensional corner on a cube). Furthermore, the echogenic material may comprise the passive ultrasonic device itself, such as when the device is manufactured from a material exhibiting echogenic properties.

Given these definitions, the devices 410 and 430 may comprise one of three combinations, namely active/active, active/passive, and passive/active. If both device 410 and 430 are active ultrasonic devices (active/active), each active ultrasonic device 410 and 430 may, in turn, include transducers 412 and 432 that are either transmitters, receivers, or both.

If both transducers 412 and 432 are transmitters and receivers, two fields of view 416, 434 are generated as illustrated in FIG. 22B. Device 410 has a field of view 416 and device 430 has a field of view 434. The fields of view 416 and 434 may be superimposed to generate a highly accurate image.

If transducers 412 and 432 are a receiver and a transmitter, respectively, the transmitting transducer 432 acts as a beacon to the receiving transducer 412. Of course, the transmitting transducer may be switched with the receiving transducer such that transducer 412 becomes the beacon to transducer 432.

An example of an active/passive combination is when device 410 includes a transmitting and receiving transducer 412 and device 430 includes an echogenic material 432. With this arrangement, the passive transducer 432 highlights the target location as monitored by the active transducer 412. Of course, device 430 may be active and device 410 may be passive.

Each of these embodiments, whether utilizing active/active, active/passive or passive/active ultrasonic device combinations, facilitate the navigation and orientation of the tissue penetrating member as the extravascular openings and pathway are created as seen by the IVUS image.

Figure 23A:
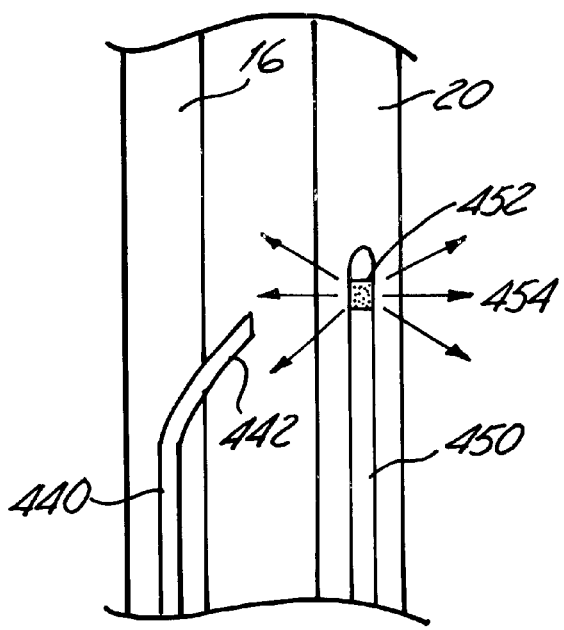
FIGS. 23A and 23B are side views of a distal portion of a tissue penetration monitoring device disposed in the coronary vasculature in accordance with another embodiment of the present invention.
Figure 23B:
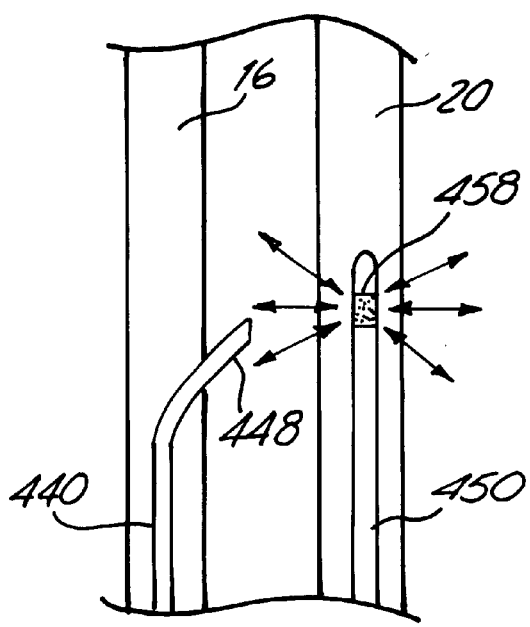

FIGS. 23A and 23B illustrate side views of a distal portion of tissue penetration alignment and monitoring devices 440 and 450 disposed in the coronary vasculature 16, 20 in accordance with another embodiment of the present invention. Although not shown on the devices 440 and 450, it is contemplated that an alignment marker comprising an echogenic material may be utilized as stated previously. In FIG. 23A, active ultrasonic device 440 in the form of a tissue penetrating member includes a ultrasonic transducer 442 adapted to receive ultrasonic signals 454 emitted from ultrasonic transmitting transducer 452 of device 450. Device 450 is in the target lumen (e.g., coronary vein 20) and device 440 is in the native lumen (e.g., coronary artery 16). In this embodiment, the ultrasonic transmitting transducer 452 acts as a beacon to ultrasonic receiving transducer 442 on device 440. With this arrangement, the tissue penetrating member 440 may be advanced in the direction of the device 450 as guided by the beacon signals 454.

The embodiment illustrated in FIG. 23B is similar to the embodiment illustrated in FIG. 23A, except that device 440 is a passive ultrasonic device incorporating an echogenic material 448. In addition, the transducer 458 on device 450 is a transmitting and receiving transducer which transmits signals and receives signals reflected off of echogenic material 448 on device 440. In this embodiment, transducer 458 monitors the advancement of echogenic material 458 on the penetrating member 440 as it passes from the native lumen to the target lumen.

Figure 24A:
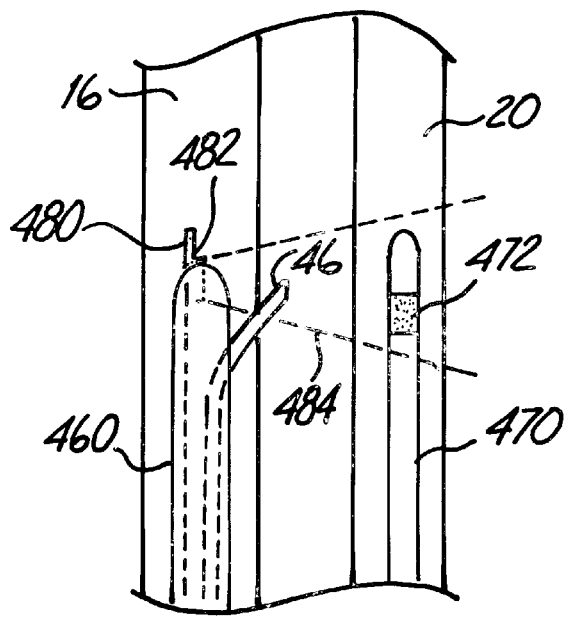
FIGS. 24A and 24B are side views of a distal portion of a tissue penetration monitoring device disposed of the coronary vasculature in accordance with yet another embodiment of the present invention.
Figure 24B:
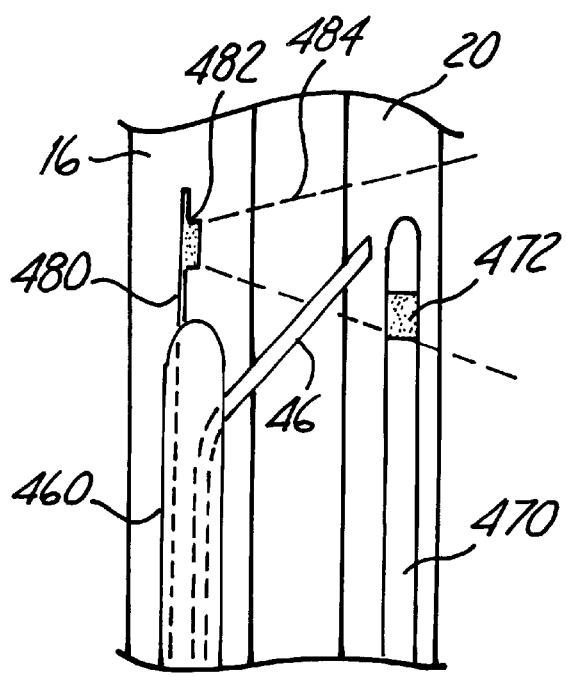

FIGS. 24A and 24B illustrate a side view of a distal portion of tissue penetration alignment and monitoring devices 460 and 470 disposed in the coronary vasculature 16, 20 in accordance with yet another embodiment of the present invention. Device 460 includes a tissue penetrating member 46 slidably disposed therein. In addition, device 460 includes an intravascular ultrasound device 480 in the form of a wire or catheter. The IVUS device 480 is slidably disposed in the tissue penetration alignment and monitoring device 460. IVUS catheter 480 includes an ultrasonic transmitting and receiving transducer 482 having a directional or rotational field of view 484.

The IVUS device 480 may be advanced or retracted to align the transducer 482 with the distal end of the tissue penetrating member 46. In this manner, the position of the distal end of the tissue penetrating member 46 may be monitored as it creates an extravascular opening in the coronary artery 16, creates the pathway between the artery 16 and the vein 20, and creates the extravascular opening in the vein 20 as shown in FIG. 24B.

It is contemplated that the IVUS device 480 may be advanced in conjunction with the tissue penetrating device 46 to monitor its progress as it passes from the coronary artery 16 to the coronary vein 20. Alternatively, the IVUS device 480 may be positioned such that the field of view 484 is aligned with the target location and the tissue penetrating member 46 is advanced until the distal end thereof is visible in the field of view 484.

In both of these embodiments, the tissue penetration and monitoring device 460 may be used independently of device 470 in the target lumen. However, if it is desired to accurately mark the target lumen, device 470 having echogenic marker 472 may be utilized. In this manner, the relative position between the tissue penetrating member 46 (which is made of an echogenic material) and the echogenic marker 472 on the device 472 may be monitored. It is further contemplated that the target vessel itself may be marked with an echogenic material. The target vessel may be so marked utilizing an echogenic coating such as microbubbles applied to the inner wall of the target vessel or by implanting a device such as a stent incorporating echogenic material.

FIGS. 25A–25E illustrate tissue penetrating guiding devices 500, 502 for bypass operation. As shown, device 500 includes an elongated shaft 504, a flexible tip 506 and a magnetic member 508. Device 502 includes an elongated shaft 510 having a distal end portion 512 formed of a magnetic material and including a guide conduit 516 having traverse opening 518, an axial end opening 520 and a flexible tip 522.

In the embodiment shown, device 500 is insertable into artery 16 and device 502 is insertable into vein 20. Distal portion 514 of device 502 is inserted to align opening 518 relative to a puncture or bypass site through the vessel wall as shown in FIG. 25C to form a guiding device for a penetrating member. Device 500 is inserted to align tip 506 relative to distal portion 512 of device 502. Magnetic member 508 and magnetic distal end portion 512 are magnetically attractable for locating and guiding bypass operating devices (e.g. penetrating device 524). As shown, device 500 includes a penetrating device lumen having a distal opening 522 proximate to magnetic member 508 and tip 506. A penetrating device 524 is inserted through lumen for placement at a penetrating site.

Figure 25A:
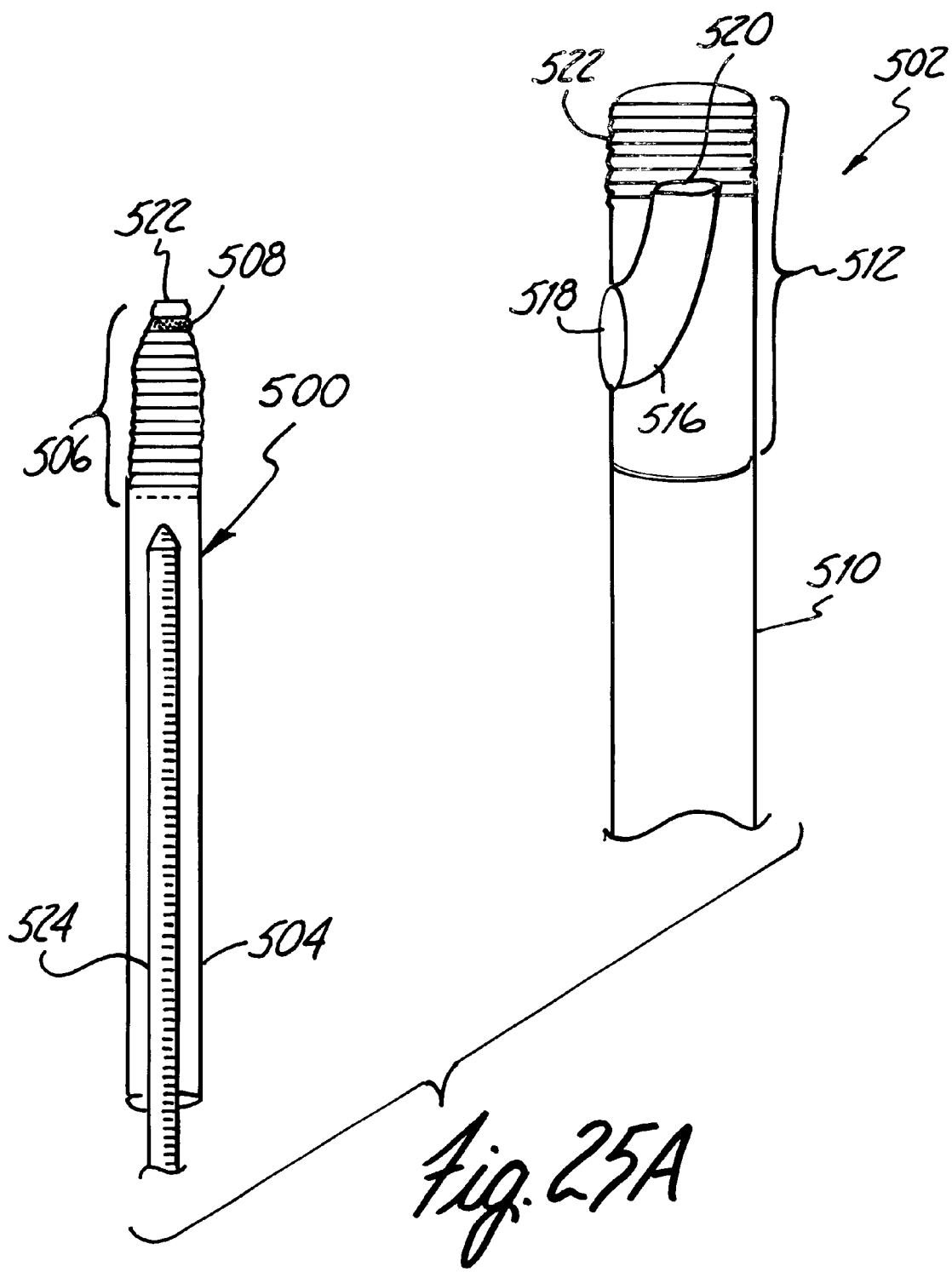
FIGS. 25A–25E illustrate an embodiment of a tissue penetration guide device.
Figure 25B:
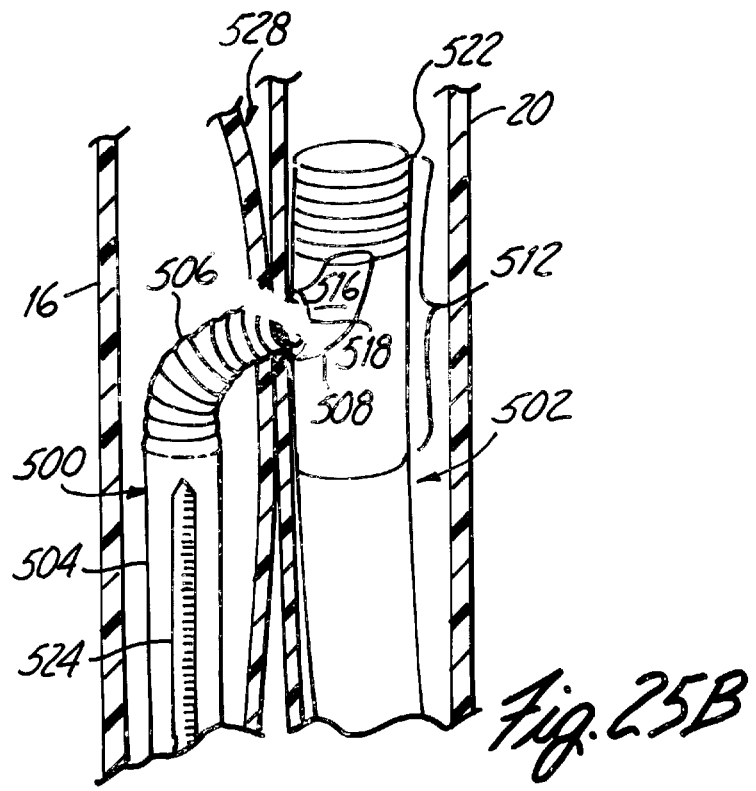
Figure 25C:
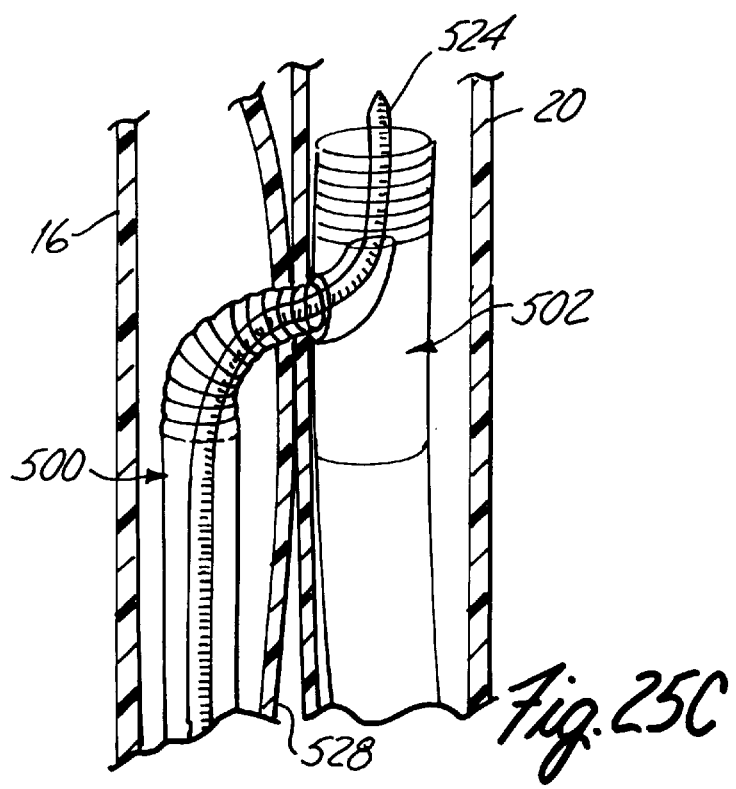
Figure 25D:
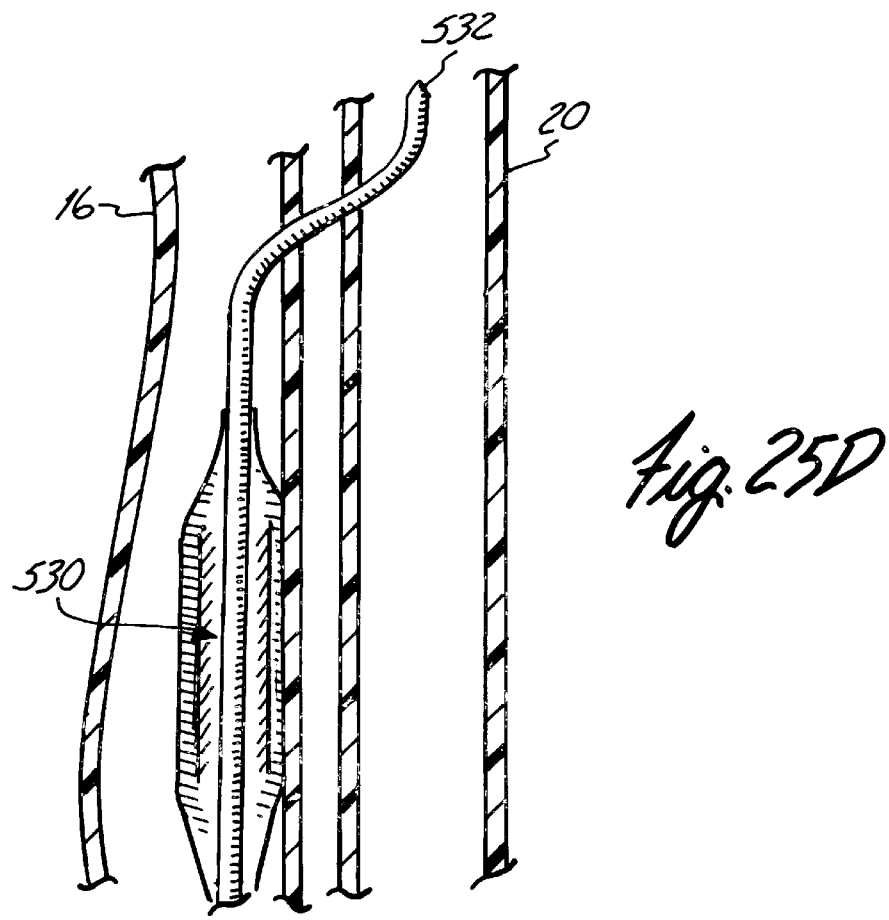
Figure 25E:
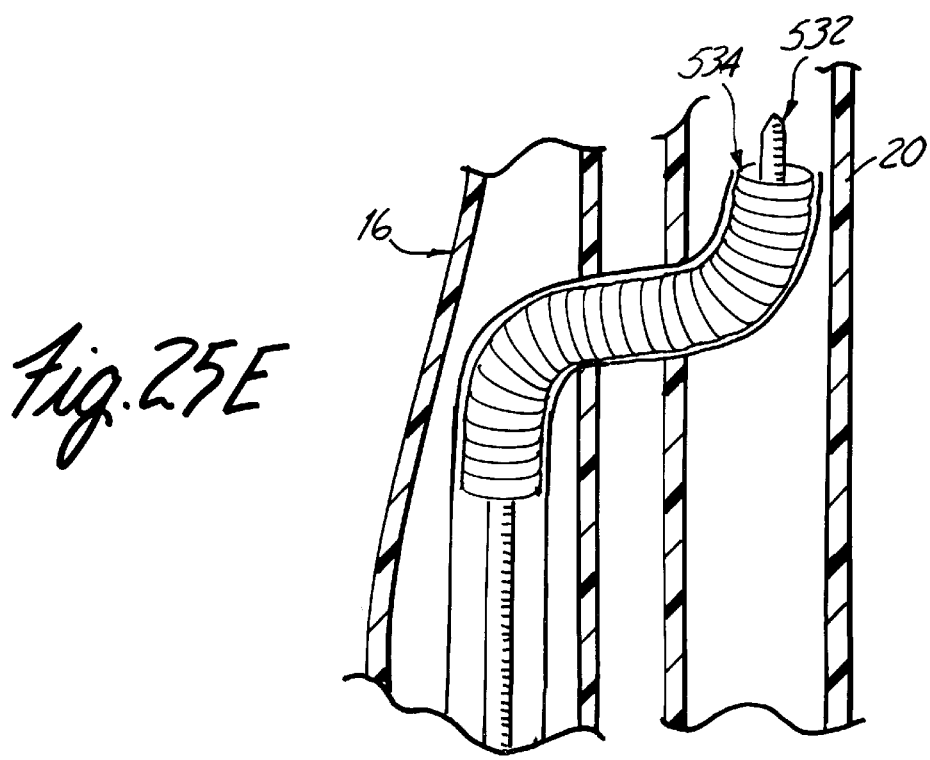
Figure 251:
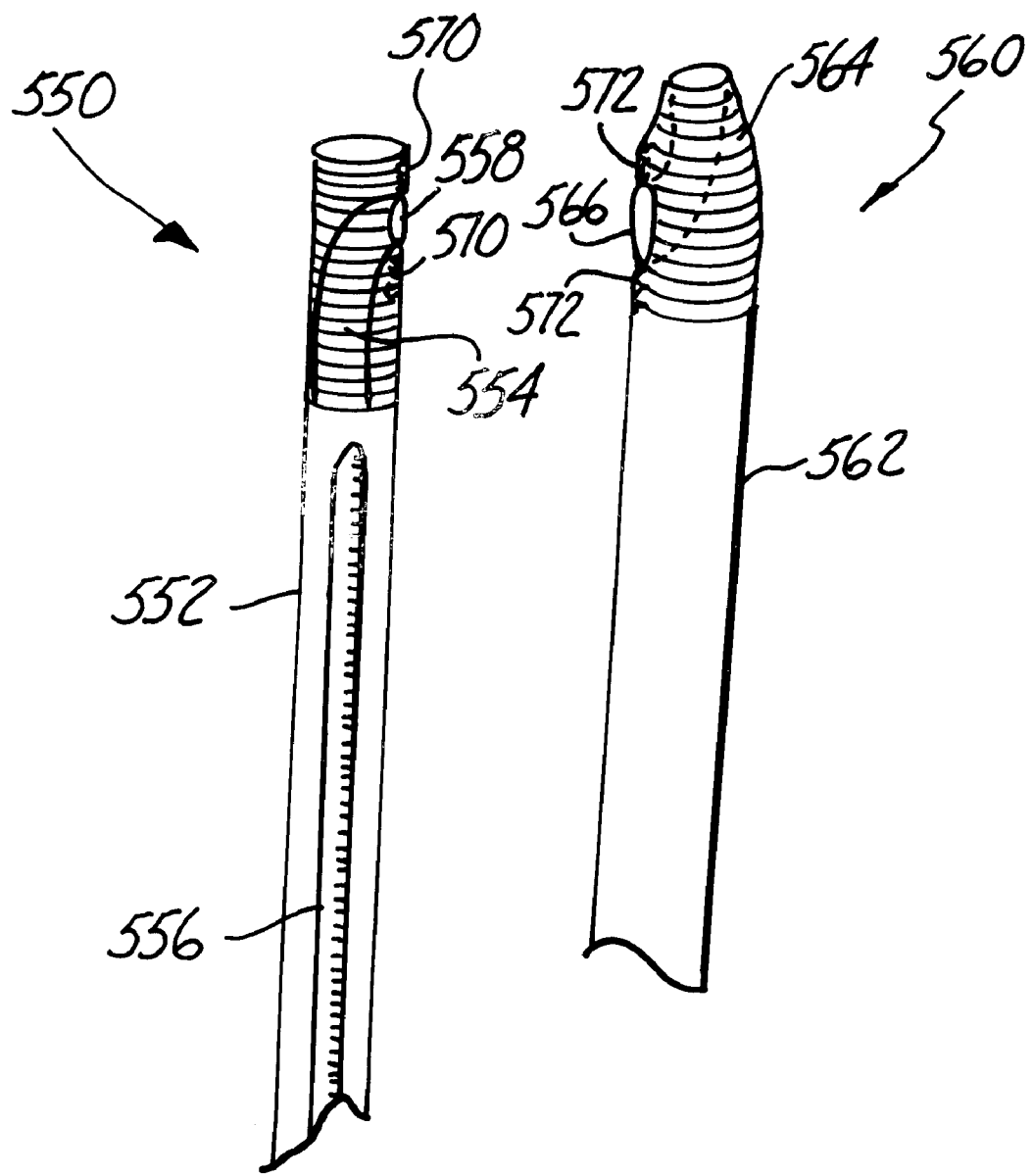

For operation as shown in FIG. 25B, opening 522 is aligned with opening 518 via magnetic attraction of member 508 and distal portion 512. Thereafter, as progressively shown in FIGS. 25B–C, penetrating device 524 is advanced to the puncture site to pierce the arterial wall 528. Penetrating device 524 is guided through lumen of device 500 and conduit 516 to maintain hemostasis while penetrating or piercing vessel walls. Thereafter, as illustrated in FIGS. 25D–25E, penetrating member may be withdrawn and a stent delivery device 530 may be advanced over a guidewire 532 previously inserted for deployment of a bypass stent 534 as previously explained.

Preferably, magnetic member 508 and distal magnetic portion 512 are permanent magnets formed of a neo-dynium material, boron, Hiperco alloy 50 or other ferrous material. Although, as illustrated, device 500 is inserted into artery 16 and device 502 is inserted into vein 20, application is not so limited to the exact embodiment shown and described. An alternate embodiment is illustrated in FIG. 25F. As shown, device 550 includes a shaft 552 having a penetrating lumen 554 for a penetrating device 556 and a transverse lumen opening 558. Device 560 includes an elongated shaft 562 and a distal conduit 564 including a transverse opening 566 and an axial end opening 568. Device 550 is insertable into artery 16 and device 560 is insertable into vein 20. Opening 566 of conduit 564 is aligned with a puncture site. Opening 558 is aligned with conduit 564 and opening 566 for locating and guiding penetrating device 556. Opening 558 is aligned with opening 566 via permanent magnets 570, 572 positioned about openings 556, 558.

Although the present invention has been described with reference to preferred embodiments, workers skilled in the art will recognize that changes may be made in form and detail without departing from the spirit and scope of the invention.

What is claimed is:

1. An intravascular catheter for creating an extravascular opening in a vessel wall, comprising:

an elongate shaft having a proximal end and a distal end, the shaft adapted for intravascular navigation;

an anchoring mechanism disposed on the distal end of the shaft, the anchoring mechanism having a delivery position and an anchor position;

a tissue penetrating member having a proximal end and a distal end, the proximal end of the penetrating member slidably disposed in the shaft and the distal end of the tissue penetrating member having a tissue penetrating mechanism, wherein the tissue penetrating member is extendable between a retracted position and a penetrating position, the tissue penetrating mechanism extending completely through the vessel wall when in the penetrating position to establish the extravascular opening therethrough and the tissue penetrating member including a flexible normally curved tip; and a relatively stiff tubular member slidably disposed relative to the tissue penetrating member to adjust flexure of the flexible normally curved tip of the penetrating member.

2. An intravascular catheter as in claim 1 further comprising:

a stiffening member disposed about the tissue penetrating member between the relatively stiff tubular member to provide rigidity to a distal portion of the tissue penetrating member.

3. An intravascular catheter as in claim 1, wherein the anchoring mechanism comprises an inflatable balloon.

4. An intravascular catheter as in claim 3, further comprising an outer tube in which the tissue penetrating member is disposed and through which the relatively stiff tubular member slidably extends.

5. An intravascular catheter as in claim 4, wherein the outer tube terminates adjacent a distal cone of the balloon between a proximal end and a distal end of the balloon.

6. An intravascular catheter as in claim 4, wherein the outer tube terminates adjacent a proximal cone of the balloon between a proximal end and a distal end of the balloon.

7. An intravascular catheter as in claim 4, wherein the outer tube terminates adjacent a body portion of the balloon between a proximal end and a distal end of the balloon.

8. An intravascular catheter as in claim 4, wherein the outer tube exits a distal end of the balloon.

9. An intravascular catheter as in claim 4 wherein the balloon is separated into a proximal balloon and a distal balloon and wherein the outer tube terminates between balloons.

10. An intravascular catheter as in claim 4 wherein the balloon comprises a helical type balloon and wherein the outer tube terminates at a mid portion of the helical type balloon.

11. An intravascular catheter as in claim 2, wherein the distal end of the tissue penetrating member is at an angle relative the shaft when in the penetrating position.

12. An intravascular catheter as in claim 5, wherein the angle is up to 90°.

13. An intravascular catheter as in claim 1, wherein the anchoring mechanism comprises an inflatable balloon and the tissue penetrating member extends through a lumen along the elongate shaft and the lumen includes a portion extending along a length of the inflatable balloon to a distal lumen opening between a proximal end and a distal end of the inflatable balloon and the tissue penetrating member is slidably extendable through the distal lumen opening so that the distal end of the tissue penetrating member exits the anchoring mechanism.

14. An intravascular catheter as in claim 1, further comprising a stiffening member slideable relative to the shaft and the relatively stiff tubular member is disposed about the stiffening member.

15. A method of bypassing a restriction in a vessel, comprising the steps of:
providing an intravascular catheter having a tissue penetrating member disposed therein, a proximal end of the penetrating member slidably disposed in the catheter and a distal end of the tissue penetrating member having an adjustable tip portion having an adjustable orientation and the adjustable tip portion including a tissue penetrating mechanism;
navigating a distal end of the catheter to a position adjacent the restriction;
remotely adjusting the orientation of the adjustable tip portion of the tissue penetrating member; and
slidably advancing the tissue penetrating member relative to the catheter to form an extravascular passageway.

16. A method of bypassing a restriction in a vessel as in claim 15, wherein the catheter includes an anchor mechanism, further comprising the steps of:
prior to advancing the tissue penetrating member, actuating the anchor mechanism such that the anchor mechanism is anchored adjacent the restriction in the vessel.

17. A method of bypassing a restriction in a vessel as in claim 16, wherein the anchor mechanism comprises a balloon, and wherein the step of actuating the anchor mechanism comprises the step of inflating the balloon.

18. A method of bypassing a restriction in a vessel as in claim 15, further comprising the steps of:
emitting light from the distal end of the penetrating member; and
detecting light reflected by tissue adjacent the distal end of the penetrating member to monitor advancement of the tissue penetrating member.

19. A method of bypassing a restriction in a vessel as in claim 15, further comprising the steps of:
emitting ultrasound from the distal end of the penetrating member; and
detecting ultrasound reflected by tissue adjacent the distal end of the penetrating member to monitor advancement of the tissue penetrating member.

20. A method of bypassing a restriction in a vessel as in claim 15, further comprising the steps of:
emitting light from the distal end of the penetrating member; and
detecting light emitted from the distal end of the penetrating member in a lumen of an adjacent vessel to monitor advancement of the tissue penetrating member.

21. A method of bypassing a restriction in a vessel as in claim 15, further comprising the steps of:
emitting ultrasound from the distal end of the penetrating member; and
detecting ultrasound emitted from the distal end of the penetrating member in a lumen of an adjacent vessel to monitor advancement of the tissue penetrating member.

22. A method of bypassing a restriction in a vessel as in claim 15, wherein the tissue penetrating mechanism creates an opening in a wall of the vessel, further comprising the steps of:
providing a thermal energy emitter for heat fusing the opening;
navigating the thermal energy emitter to the opening; and
heat fusing the opening.

23. A method of bypassing a restriction in a vessel as in claim 22, wherein the thermal energy emitter comprises a heatable balloon, further comprising the steps of:
inflating the heatable balloon in the opening;
activating the heatable balloon so as to heat the opening; and
deflating the heatable balloon.

24. A method of bypassing a restriction in a vessel as in claim 15 comprising the steps of:
emitting light from a bypass position in a first vessel to illuminate a bypass site proximate to the restriction; and
detecting light illuminated from the first vessel in a second vessel by a sensor proximate to the distal end of the penetrating member to monitor a position of the tissue penetrating member.

25. A method of bypassing a restriction comprising the steps of:
providing an intravascular catheter including a tissue penetrating member slideably disposed in the catheter and including a tissue penetrating mechanism at a distal tip of the tissue penetrating member;
navigating the catheter through a vessel proximate to a restriction to form an extravascular passageway between body vessels;
slidably advancing the tissue penetrating member relative to the intravascular catheter to form the extravascular passageway and injecting radiopaque contrast media through a lumen of the penetrating member; and
observing the penetrating member and the contrast media under fluoroscopy to monitor advancement of the penetrating member to form the extravascular passageway between the body vessels.

26. A method of bypassing a restriction comprising the steps of:
providing an intravascular catheter including a tissue penetrating member slideably disposed relative to the intravascular catheter and including a tissue penetrating mechanism proximate to a distal end of the penetrating member;
navigating the catheter through a vessel proximate to the restriction and slidably advancing the tissue penetrating member to form an extravascular passageway between body vessels;
measuring pressure at the distal end of the penetrating member; and
observing the pressure as the penetrating member penetrates a wall of the vessel to monitor advancement of the penetrating member to form the extravascular passageway between the body vessels.

27. An intravascular device comprising:

an elongated shaft having a proximal end and a distal end and having a first inflation lumen extending therethrough;

an inflatable balloon having a proximal end and a distal end and an inflatable portion open to the inflation lumen;

a second lumen having a proximal end and a distal end and extending along a length of the elongated shaft and along a length portion of the inflatable balloon and having a distal opening between the proximal and distal ends of the inflatable balloon; and a tissue penetrating member having a tissue penetrating mechanism slidably disposed through the second lumen and having a tip portion extending through the distal opening between the proximal and distal ends of the inflatable balloon.

28. The intravascular catheter of claim 27 wherein the balloon is an eccentric balloon and the second lumen is formed by a separate channel along the length portion of the balloon.

29. The intravascular catheter of claim 28 herein the second lumen is formed through a tube extending along the length of the elongated shaft and along the length portion of the inflatable balloon.

30. The intravascular catheter of claim 27 wherein the balloon is a helical balloon supported by a balloon sheath and the second lumen is formed through a tube extending along the length of the elongated shaft and along a portion of the balloon sheath and the tube having a distal opening forming the distal opening of the second lumen between the proximal and distal ends of the balloon.

31. An intravascular catheter comprising:

an elongated shaft having a proximal end and a distal end and an elongated length therebetween;

a tissue penetrating member having a proximal end and a distal end and slidably coupled to the elongated shaft to move between a first position and a second extended position and the tissue penetrating member including a tissue penetrating mechanism and an adjustable distal tip portion having an adjustable orientation; and a distal tip actuator including a distal portion operably coupled to the distal tip portion of the tissue penetrating member and an external control portion remote from the distal tip portion and operable to adjust the distal tip portion of the tissue penetrating member in a plurality of orientations.

32. The intravascular catheter of claim 31 wherein the distal tip actuator includes an elongated wire extending along the elongated length of the elongated shaft and the wire having a distal portion coupled to the distal tip portion of the tissue penetrating member and a proximal portion remote from the distal portion to adjust the distal tip portion of the tissue penetrating member in the plurality of orientations.

33. The intravascular catheter of claim 32 wherein the wire is coupled to a tubular member having an bendable tip segment disposed about the tissue penetrating member and the wire is coupled to the bendable tip segment to adjust the orientation of the distal tip portion of the tissue penetrating member.

34. The intravascular catheter of claim 33 and further comprising a stiffener member slidably disposed relative to the shaft and positioned between the tissue penetrating member and the tubular member.

35. The intravascular catheter of claim 33 wherein the wire is coupled to the bendable tip segment through a tubular collar.

* * * * *